United States Patent [19]
Jones

[11] Patent Number: 5,411,875
[45] Date of Patent: May 2, 1995

[54] METHOD FOR RETRIEVAL OF UNKNOWN FLANKING DNA SEQUENCE

[75] Inventor: Douglas H. Jones, Iowa City, Iowa

[73] Assignee: University of Iowa Research Foundation, Oakdale, Iowa

[21] Appl. No.: 786,902

[22] Filed: Nov. 1, 1991

[51] Int. Cl.⁶ .............................................. C12P 19/34
[52] U.S. Cl. ........................................ 435/91.2; 435/6; 435/91.1; 435/810; 536/22.1; 536/24.2; 536/24.3; 935/77; 935/78; 935/88
[58] Field of Search .................. 435/6, 91, 810, 91.1, 435/91.2; 436/501; 536/27-29, 22.1, 23.1, 24.2, 24.3; 935/78, 88, 77

[56] References Cited

PUBLICATIONS

Jones et al. (1992) Nucleic Acids Research, vol. 20, No. 3, pp. 595–600.
Cariello et al. (1991) Gene, vol. 99, pp. 105–108.

*Primary Examiner*—Margaret Parr
*Assistant Examiner*—Ardin H. Marschel
*Attorney, Agent, or Firm*—Frederick W. Pepper

[57] ABSTRACT

A method that permits the highly specific PCR amplification of unknown DNA that flanks a known sequence region. In this method, known DNA is placed on the uncharacterized side of that specific sequence that contains the unknown DNA by a DNA polymerase mediated generation of a PCR template that is shaped like a pan with a handle. Generation of this template permits specific amplification of the segment of interest.

52 Claims, 17 Drawing Sheets

4. Add primers 1 and 2.

5. PCR amplify.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GATCTTCTCT GTCTCCACAT GCCCAGTTTC TATTG          35

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGGCCCTGGC AGGTTGGTAT C          21

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCCTCTTGGG TTTCTGATAG GCACTGAC          28

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CAAGGTTACA AGACAGGTTT AAGGAGAC          28

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGTCTCTCTG CCTATTGGTC TATTTTCC    28

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CTAGTTCTCT GTCTCCACAT GCCCAGTTTC TATTG    35

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AGCTTGAGCC CAGACGGCCC TAGCAGGGAC    30

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TTTGGAGACA CCGCTGGCCT TTTC    24

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTAATGCCAA AGACCTACTA CTCTGGGTGC    30

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGGCGACCTC TGCATGGTCT CTC    23

( 2 ) INFORMATION FOR SEQ ID NO:11:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

GCTGCCGCTC AACCCTTTTT CTCTG  25

( 2 ) INFORMATION FOR SEQ ID NO:12:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

GCACTCTAGA GAGACGACTT GACACTGGAC ACGTGAGATC GTCCAGTGTC AAGTCGTC  58

( 2 ) INFORMATION FOR SEQ ID NO:13:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GCACTCTAGA GAGACGACTT GACACTGGAC ACGTGAGATC CTGCTGAACT GTGACCTG  58

METHOD FOR RETRIEVAL OF UNKNOWN FLANKING DNA SEQUENCE

FIELD OF THE INVENTION

The present invention relates to a method for the retrieval of an unknown DNA sequence that flanks a known DNA sequence. More particularly, this method eliminates laborious cloning steps and associated cloning artifacts in obtaining DNA sequence information from complex mixtures, such as human genomic DNA. This method also permits genome walking into unclonable regions of DNA.

BACKGROUND OF THE INVENTION

PCR is a powerful method by which specific sequences of DNA can be amplified exponentially in vitro without cloning. PCR requires that primer annealing sites be present in each end of the target sequence in order for amplification to occur. Until recently, PCR has required knowledge of the sequences initially flanking the target sequence. Consequently, PCR could not be used to amplify and sequence unknown DNA flanking a known sequence. Recently, various methods have been developed that permit the amplification of sequences which flank only one known primer annealing site. These methods permit the amplification of previously uncharacterized regions of DNA. However, none of these existing methods has been shown to have sufficient specificity for widespread application for the direct sequencing of unknown DNA in human genomic DNA.

These methods that have been developed to amplify unknown flanking DNA can be divided into the following six types. The first method involves the creation of new primer annealing sites by tailing all the strands in a mixture using non-template directed DNA polymerization with one deoxyribonucleotide and terminal transferase (Frohman et al., *Proc. Natl. Acad. Sci. USA*, 85, 8998–9002, 1988; Loh et al., *Science*, 243, 217–220, 1989; Ohara et al., *Proc. Natl. Acad. Sci. USA*, 86, 5673–5677, 1989). Due to this tailing reaction, all of the strands in the mixture contain a universal primer annealing site. This site is used in conjunction with a sequence-specific primer for the PCR amplification of unknown DNA flanking a known sequence.

The second method requires ligation of linkers or plasmid sequences to the ends of restriction enzyme digested DNA strands in the original mixture (Shyamala et al., *Gene*, 84, 1–8, 1990; Hovens et al., *Nucleic Acids Res.*, 17, 4415, 1989). In both the first and second methods, the specificity of the reaction is diminished by the creation of a new primer binding site which is shared by the other sequences in the original mixture, thereby increasing the probability of unwanted products. It is not surprising, therefore, that these strategies have found little success in the specific amplification of genomic eukaryotic DNA.

In a modification of the second method, the third method adds a physical separation step in order to increase the specificity of the reaction. Ligation of linkers to the ends of restriction enzyme digested DNA is followed by primer extension with a biotinylated primer that anneals to the unique site. This is followed by separation with magnetic streptavidin (Rosenthal et al., *Nucleic Acids Res.*, 18, 3095–3096, 1990). The third method has been used for the amplification of unknown DNA from genomic eukaryotic DNA, but the length of DNA amplified has not been shown, and the overall effectiveness of this method is not clear.

The fourth method involves polymerization from a single primer site followed by ligation of a linker (subsequently used as a primer annealing site) to the opposite end of the double-stranded primer-extended product (Pfeifer et al., *Science*, 246, 810–813, 1989; Mueller and Wold, *Science*, 246, 780–786, 1989; Steigerwald et al., *Nucleic Acids Res.*, 18, 1435–1439, 1990). This method has been used to sequence a single product from human genomic DNA, but not without the complication of using the multiplex method of sequence analysis (Church and Kieffer-Higgins, *Science*, 240, 185–188, 1988). In addition, the fourth method may be limited by the efficiency of primer extension to a blunt ended product, the efficiency of blunt-end ligation, and by ligation of the linker (primer annealing site) to other double-stranded ends.

The fifth method is called vectorette PCR (Riley et al., *Nucleic Acids Res.*, 18, 2887–2890, 1990). In this method, synthetic duplexes are ligated to the restriction enzyme digested ends of DNA. The unique feature of this method lies in the construction of the synthetic duplexes, termed vectorette units. Vectorette units contain a bubble region of non-complementarity. The vectorette PCR primer is identical to one of the non-complementarity portions. The vectorette PCR primer, therefore, contains no region of complementarity to the end modified DNA unless polymerase extension is initiated from an upstream portion of a DNA strand. The DNA strand of interest is amplified to the extent that this initial DNA primer extension (from the non-vectorette primer that anneals to the known region) is specific for the strand of interest. A limiting factor with this method may be the specificity in the primer extension step that generates an annealing site for the the vectorette primer. This is because primer extension from a site near the 5' end of any DNA strand will create an annealing site for the vectorette primer, which results in a PCR product.

The sixth method called inverse PCR (Ochman et al., *Genetics*, 120, 621–623, 1988; Triglia et al., *Nucleic Acids Res.*, 16, 8186, 1988; Silver and Keerikatte, *J. Virol.*, 63, 1924–1928, 1989) permits amplification of DNA flanking a known sequence by circularization of restriction enzyme digested DNA. This permits amplification of the flanking sequence by positioning two primers, each of which binds to the known sequence "inside out" on the circle. Therefore, this strategy maintains specificity at each primer binding site. Difficulties with inverse PCR include the requirement for two restriction sites that flank the priming region and inefficient PCR amplification of closed circular DNA. This inefficient PCR amplification occurs, if a convenient restriction enzyme site is not present to linearize the circle between the 5' ends of the two amplifying primers prior to PCR amplification (Silver and Keerikatte, *J. Virol.*, 63, 1924–1928, 1989). Without linearization, double-stranded circular DNA is amplified much less efficiently than linear DNA (Jones and Howard, *BioTechniques*, 10, 62–66, 1991). Nicking the circles by heating ameliorates the difficulty in amplifying closed circular double-stranded DNA, but only a small percentage of the circles are nicked between the two 5' ends of the amplifying primers. Therefore, any increase in the initial amplification efficiency is suboptimal.

A major obstacle in using existing methods for the PCR amplification of specific sequences in genomic DNA is the occurrence of nonspecific amplification products. Under PCR conditions, the stringency of the priming (Sommer and Tautz, *Nucleic Acids Res.*, 17, 6749, 1989) is seldom high enough to generate a pure product longer than 1 kilobase (kb) in highly complex mixtures, such as in human genomic DNA. This limits both the specificity of the reaction and the length of the amplifiable DNA. Use of nested primers (Mullis et al., *Cold Spring Harbor Symposia on Quantitative Biology, Cold Spring Harbor Laboratory*, LI, 263–273, 1986; Haqqi et al., *Nucleic Acids Res.*, 16, 11844, 1988) and size selection of the regions of interest by previous Southern blotting (Ochman et al., *Genetics*, 120, 621–623, 1988; Beck and Ho, *Nucleic Acids Res.*, 16, 9051, 1988) diminish this problem. However, high background due to insufficient stringency during the PCR amplification of genomic DNA remains a significant problem. It is not surprising, therefore, that the methods to amplify unknown flanking DNA result in limited specificity, as the initial PCR amplification using these methods does not improve upon the specificity level conferred by conventional two primer PCR. Certainly, an approach that optimizes the specificity of amplification of the unknown sequence is advantageous, regardless of the other strategies used to increase specificity (nested primers, size selection, physical separation of biotinylated products with steptavidin).

One way that the present invention overcomes the limitations encountered by the known PCR amplification methods is to use only one restriction enzyme site that flanks the priming region, instead of the two restriction enzyme sites in inverse PCR. This site is contained in the unknown flanking DNA. Also, the method of the present invention does not generate the less efficiently amplified double-stranded DNA circle produced from the self-annealing and ligation reaction of inverse PCR.

Since the method of the present invention generates a single-strand template, and the placement of known DNA on the opposite end of the strand of interest requires sequence specific annealing, it yields very high specificity. Furthermore, exploitation of the known properties of a suitable DNA polymerase, in conjunction with this method, permits purification of the template in solution, rendering this method specific for the DNA of interest.

SUMMARY OF THE INVENTION

The present invention comprises a method for a primer dependent attachment of a known sequence to the uncharacterized side of a specific DNA strand which contains an unknown sequence. This permits specific PCR amplification of the unknown DNA because known sequence now flanks the strand that contains the unknown DNA. The PCR template is generated in the following manner. First, a restriction enzyme digests DNA leaving a 5' overhang. Second, a single-stranded oligonucleotide is ligated to the restriction enzyme digested DNA. This oligonucleotide is constructed to be complementary to the known region of DNA upstream from the unknown region of DNA. Third, denaturation and self-annealing under dilute conditions results in strands of DNA, containing the complement to the ligated piece, forming a single-stranded loop, or pan portion, with a double-stranded portion of an otherwise single-stranded handle, of a panhandle structure. The sequence specific annealing that constitutes the double-stranded portion can prime template-directed DNA polymerization from the ligated oligonucleotide. This polymerization results in known DNA being placed on the uncharacterized end of the unknown DNA contained in the loop. Generation of the panhandle template permits PCR amplification of the unknown DNA because known sequence now flanks the unknown DNA in those strands that contain the unknown DNA. Since the present invention leads to the generation of the panhandle template, the method of the present invention is designated herein as "panhandle" PCR.

In one embodiment, the invention relates to a method for retrieval of an unknown DNA sequence that flanks a known DNA sequence, comprising the steps of:

(a) linearizing a double-stranded DNA fragment with a restriction enzyme to yield 5' nucleotide overhang sequences, wherein the DNA fragment comprises a region of known DNA sequence and a region of unknown flanking DNA sequence to be retrieved;

(b) ligating a 5' phosphorylated single-stranded oligonucleotide whose 5' end is complementary to the cohesive ends generated in step (a) of the double-stranded DNA fragment to yield 3' nucleotide overhang sequences complementary to a sequence portion within the known sequence region of the DNA fragment, wherein the sequence portion is an annealing site for the 3' nucleotide overhang sequences;

(c) denaturing the 3' end-modified DNA fragment to produce single-stranded fragments containing the 3' nucleotide overhang sequences;

(d) intra-strand annealing of a 3' nucleotide overhang sequence to the annealing site within the known sequence region of a single-stranded fragment, wherein the single-stranded fragment is a fragment containing the annealing site located upstream (5') to the unknown flanking sequence region, to form a single-stranded loop, or pan portion, with a double-stranded portion of an otherwise single-stranded handle, of a panhandle structure;

(e) extending the recessed 3' end of the double-stranded portion of the handle with DNA polymerase to elongate the double-stranded portion of the handle of the panhandle structure; and (f) performing a polymerase chain reaction using a set of oligonucleotide primers including a primer 1 annealing to the extended 3' end strand of step (e) of the double-stranded panhandle structure and homologous to a known sequence region upstream (5') from the annealing site for the 3' nucleotide overhang sequences and a primer 2 homologous to a known sequence region both upstream (5') from the unknown flanking sequence region and downstream (3') from the annealing site for the 3' nucleotide overhang sequences.

In another embodiment, a second stage polymerase chain reaction produces a nested primer product using a second set of oligonucleotide primers including a primer 3 homologous to a known sequence region both upstream (5') from the annealing site for the 3' nucleotide overhang sequences and downstream (3') from the known sequence region homologous to primer 1 and a primer 4 homologous to a known sequence region both upstream (5') from the unknown flanking sequence region and downstream (3') from the known sequence region homologous to primer 2.

In yet another embodiment, the invention relates to a method for retrieval of an unknown DNA sequence that flanks a known DNA sequence, which method comprises step (a) to (e) mentioned above; and (f) performing a polymerase chain reaction using an oligonucleotide primer 1 annealing to the extended 3' nucleotide end strand of step (e) of the double-stranded panhandle structure and homologous to a known sequence region upstream (5') from the annealing site for the 3' nucleotide overhang sequences.

In yet another embodiment, the invention relates to a method for retrieval of an unknown DNA sequence that flanks a known DNA sequence, which method comprises step (a) to (e) mentioned above; and (f) performing a polymerase chain reaction using a set of oligonucleotide primers including a primer 1 annealing to the single-stranded loop of step (d) and complementary to a known sequence region both upstream (5') from the unknown flanking sequence region and downstream (3') from the annealing site for the 3' nucleotide overhang sequences and a primer 2 homologous to a known sequence region both upstream (5') from the unknown flanking sequence region and downstream (3') from the known sequence region complementary to primer 1, wherein primer 1 by primer extension under the double-stranded portion of the panhandle structure jumps from one region of the single-stranded loop to an adjacent region of the single-stranded loop to generate a linear template for primer 2.

In a preferred embodiment, step (e) mentioned above contains the step of incubating a mixture containing the panhandle structure with a DNA polymerase having single-stranded 3' exonuclease activity in polymerase buffer with 1–4 dNTPs.

In a final embodiment, the invention relates to a method for purification of a DNA strand by generation of a panhandle structure, comprising the steps of:

(a) linearizing a double-stranded DNA fragment with a restriction enzyme to yield 5' nucleotide overhang sequences;

(b) ligating a 5' phosphorylated single-stranded oligonucleotide whose 5' end is complementary to the cohesive ends generated in step (a) of the double-stranded DNA fragment to yield 3' nucleotide overhang sequences complementary to a sequence portion within the DNA fragment, wherein the sequence portion is an annealing site for the 3' nucleotide overhang sequences;

(c) denaturing the 3' end-modified DNA fragment to produce single-stranded fragments containing the 3' nucleotide overhang sequences;

(d) intra-strand annealing of a 3' nucleotide overhang sequence to the annealing site of a single-stranded fragment to form a single-stranded loop, or pan portion, with a double-stranded portion of an otherwise single-stranded handle, of a panhandle structure;

(e) extending the recessed 3' end of the double-stranded portion of the handle with DNA polymerase to elongate the double-stranded portion of the handle of the panhandle structure; and (f) incubating a mixture containing the panhandle structure with a DNA polymerase having single-stranded 3' exonuclease activity in polymerase buffer with 1–4 dNTPs; or (g) incubating a mixture containing the panhandle structure of step (d) with a DNA polymerase having single-stranded 3' exonuclease activity in polymerase buffer with 1–4 dNTPs.

An object of the present invention is to develop a method that permits the PCR amplification and large-scale sequencing of unknown DNA flanking a known site in human genomic DNA.

Another object of the present invention is to develop a superior method for the construction of overlapping sets of cloned DNA, or closely spaced, unambiguously ordered, DNA markers, with continuity over lengths of at least 2 million base pairs.

Thus, the present invention overcomes major obstacles in the human genome project and has a myriad of applications in molecular biology, including: determination of viral integration sites, determination of transposon integration sites, amplification of fragments adjacent to cDNA such as regulatory regions and intron-exon junctions, generation of yeast artificial chromosome (YAC) (Burke et al., *Science*, 236, 806–812, 1987) endpoints, and chromosome jumping (Collins et al., *Proc. Natl. Acad. Sci. USA.*, 81, 6812–6816, 1984; Poustka et al., *Trends in Genet.*, 2, 174–179, 1986).

BRIEF DESCRIPTION OF THE DRAWINGS

These and various other objects, features and many of the attendant advantages of the invention will be better understood upon a reading of the following detailed description when considered in connection with the accompanying drawings wherein:

FIGS. 2—1 and 2—2 are a schematic representation of a method to amplify genomic DNA flanking a known sequence without cloning, using one primer panhandle PCR.

FIGS. 3—1 and 3—2 are a schematic representation of a method to amplify genomic DNA flanking a known sequence without cloning, using panhandle inverse PCR.

FIGS. 4—1 and 4—2 are a schematic representation of a method to purify a panhandle template with a DNA polymerase having single-stranded 3' exonuclease activity.

DETAILED DESCRIPTION OF THE INVENTION

As shown in FIGS. 1, 2, 3, and 4, the PCR template is generated following digestion of genomic DNA with a restriction enzyme that leaves a 5' overhang and ligation of a single-stranded oligonucleotide to the restriction enzyme digested genomic DNA, resulting in modification of the 3' end of each strand of the genomic digest. This oligonucleotide is constructed to be complementary to the known region of DNA upstream to the unknown region of interest. Denaturation and annealing under dilute conditions, such that intra-strand annealing is promoted, results in strands of genomic DNA, which contain the complement to the ligated piece, forming a single-stranded loop, or pan portion, with a double-stranded portion of an otherwise single-stranded handle, of a panhandle structure. The sequence-specific annealing that constitutes the double-stranded portion contains a recessed 3' end, so that this oligonucleotide can prime DNA polymerization using the known sequence as the template. This polymerization places known DNA on the uncharacterized end of the unknown DNA contained in the loop. The effect of the polymerization is to generate the panhandle template used for subsequent PCR amplification. Since the generation of the panhandle template results in the known DNA with primer sites being positioned on both sides of the unknown flanking DNA, PCR can be used to amplify the unknown DNA.

Figure 1:
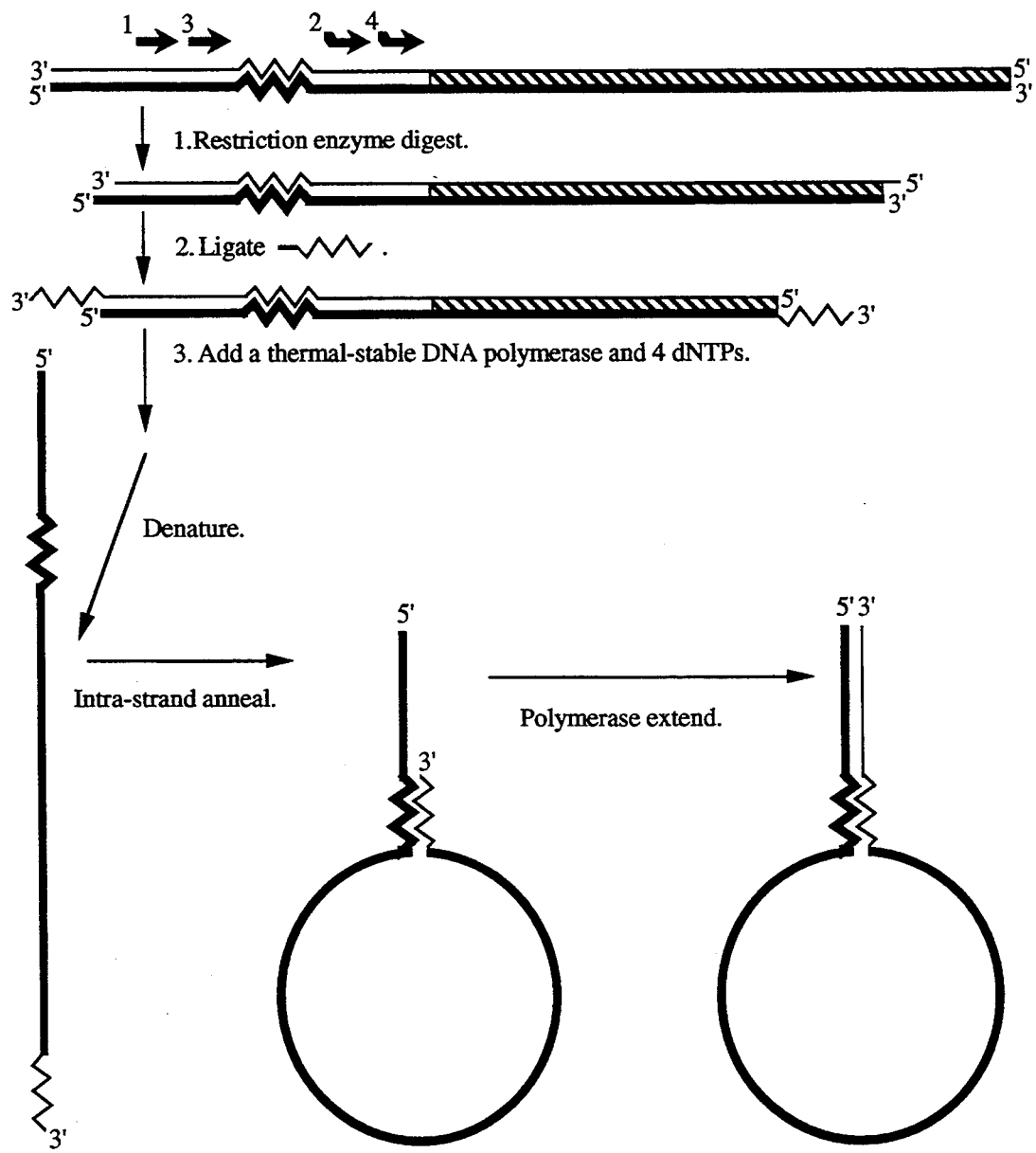
FIGS. 1—1 and 1—2 are a schematic representation of a method to amplify genomic DNA flanking a known sequence without cloning, using two primer panhandle PCR. The two complementary strands of genomic DNA are represented by thin and thick lines. Double-stranded unknown DNA that flanks the known region of genomic DNA is striped between the two strands. The jagged portion of the thick line represents the annealing region for the ligated-oligonucleotide. The PCR primers are numbered arrows. Their location in relation to the relevant strands of genomic DNA are shown on top of the diagram for step 1 in FIG. 1. The primers are not used until step 4 of the diagram in FIG. 1. Primers 2 and 4 can have 1 to 30 nucleotides added to their 5' ends that are not homologous to the thick strand of the relevant region of genomic DNA. Their upended 5' ends reflect this modification. This modification is done to decrease the possibility of a short circuit in the PCR amplification, resulting from PCR primer annealing to the thick strand of unknown flanking DNA yielding a short product. Primers 3 and 4 can be used in a nested primer PCR amplification, as shown in step 7 of the diagram.

One embodiment of the invention uses two primers (primers 1 and 2) in a PCR amplification, as shown in FIG. 1. In this embodiment primer 1 is homologous to the sequence region upstream from the annealing site for the ligated-oligonucleotide, and primer 2 is homologous to a sequence region located between the ligated-oligonucleotide annealing site and the unknown flanking DNA. Implementation of the method illustrated in FIG. 1, using two primers (primers 1 and 2) for an initial PCR amplification and two nested primers (primers 3 and 4) (Mullis et al., Cold Spring Harbor Symposia on Quantitative Biology, Cold Spring Harbor Laboratory, LI, 263–273, 1986) in a subsequent PCR amplification, permits consistent amplification and sequencing of DNA directly from the human genome. Initially, such DNA flanked one side of the primer annealing sites.

Figures 1, 2:
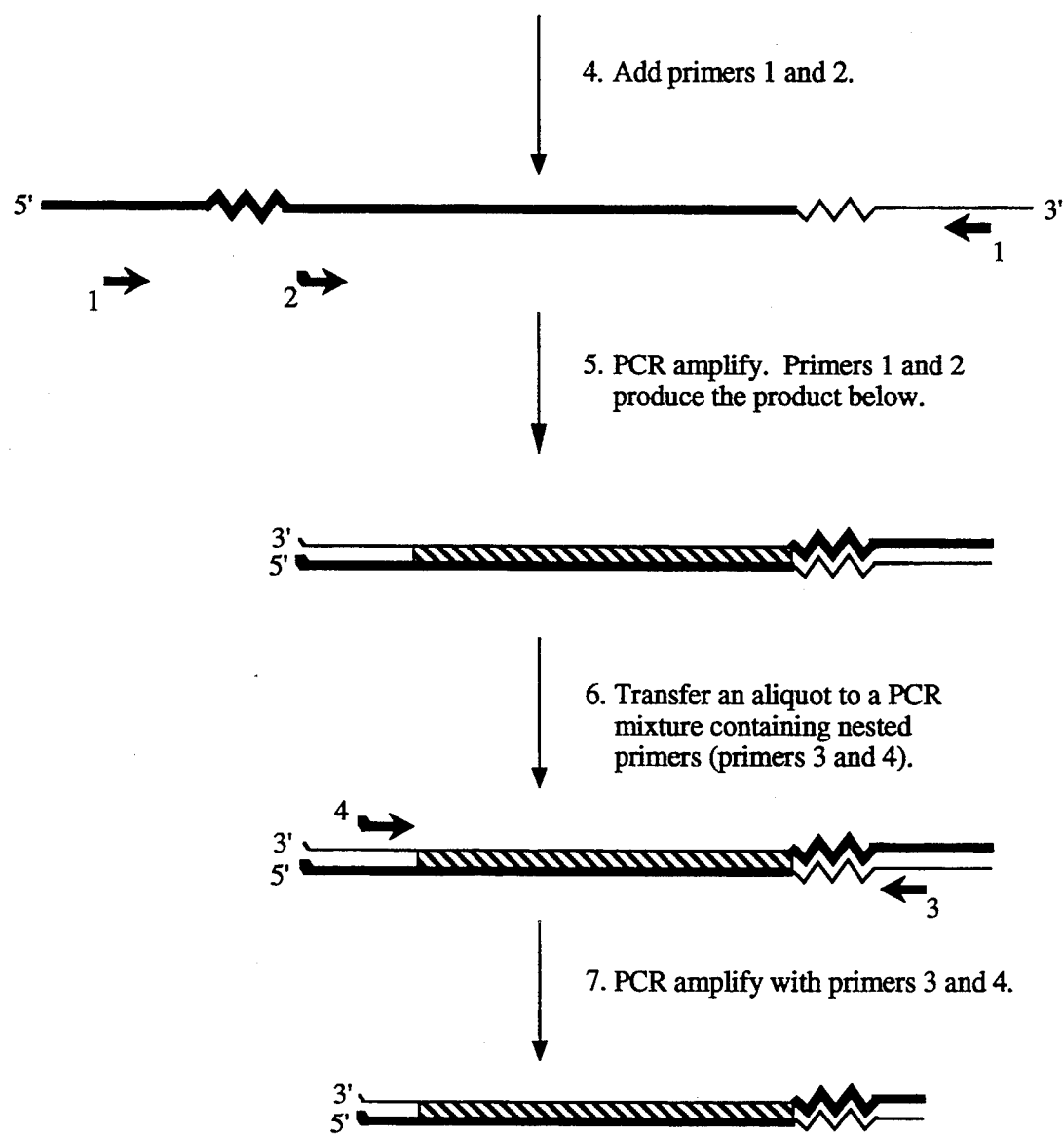
Figures 1, 2:
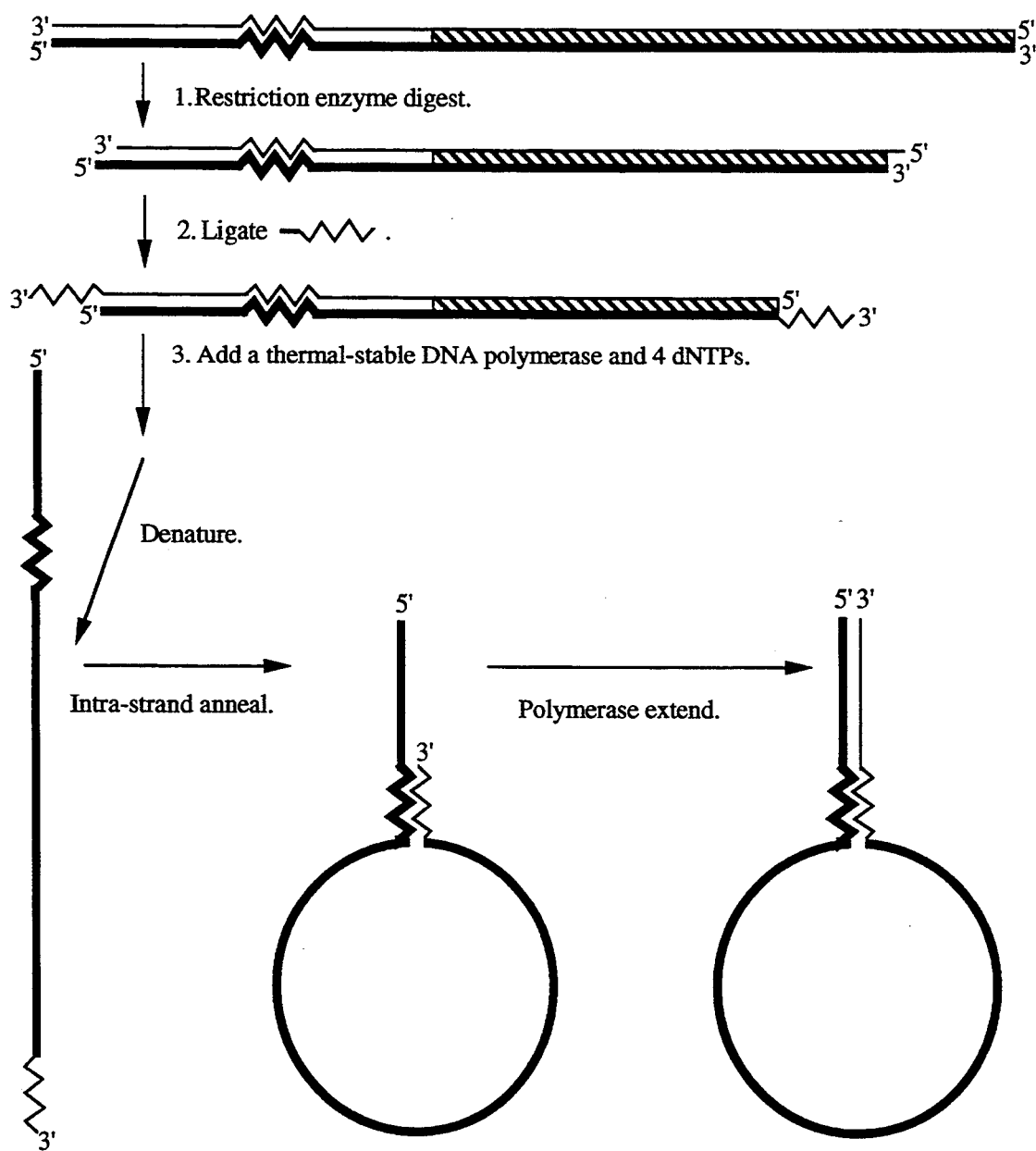
Figure 2:
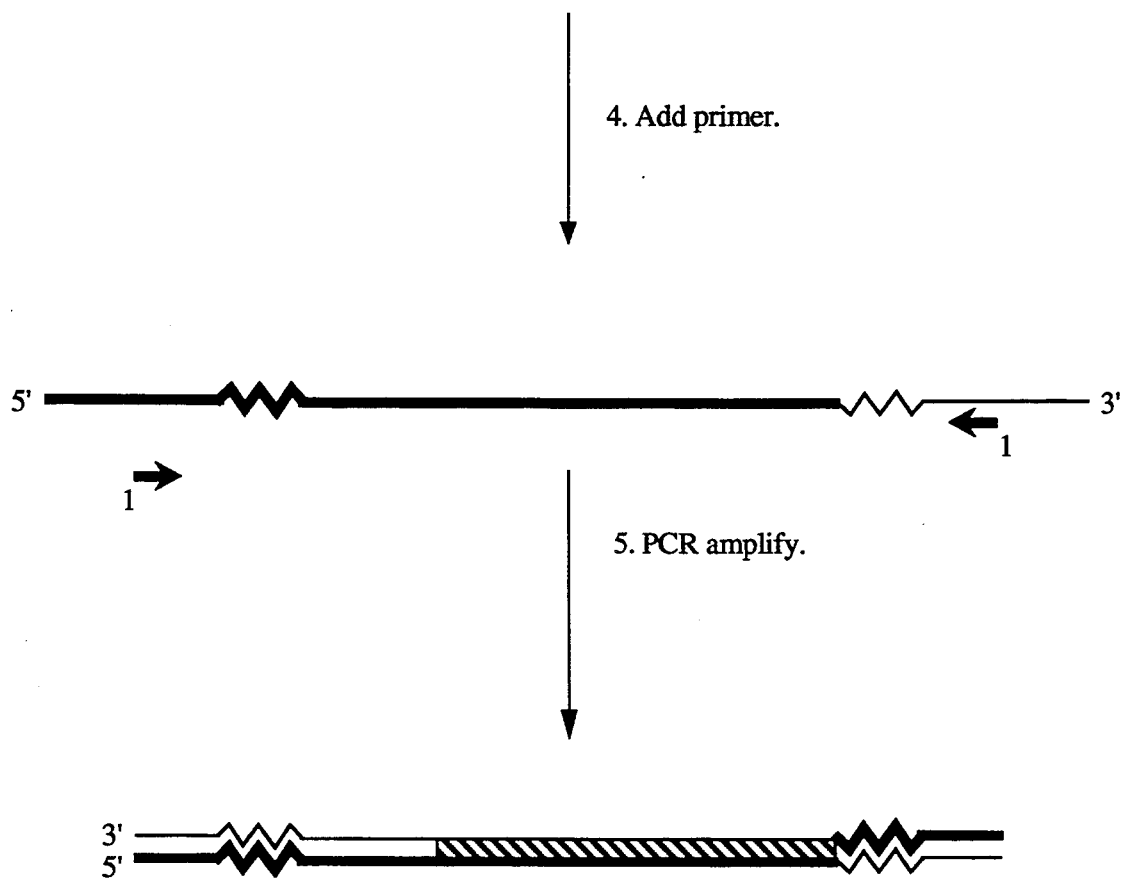

Another embodiment of the invention uses one primer (primer 1) in a PCR amplification, as shown in FIG. 2. In this embodiment primer 1 is homologous to the sequence region upstream from the annealing site for the ligated-oligonucleotide. Following PCR amplification with primer 1, if necessary, a second nested primer is used alone, which anneals internally to primer 1 on each end of the PCR product. The second primer also anneals to the inverted repeat sequence generated during the formation of the double-stranded panhandle template, and does not anneal to the ligated oligonucleotide, which is shared by numerous strands. In this manner, one obtains a nested primer product with only one primer.

Figures 1, 3:
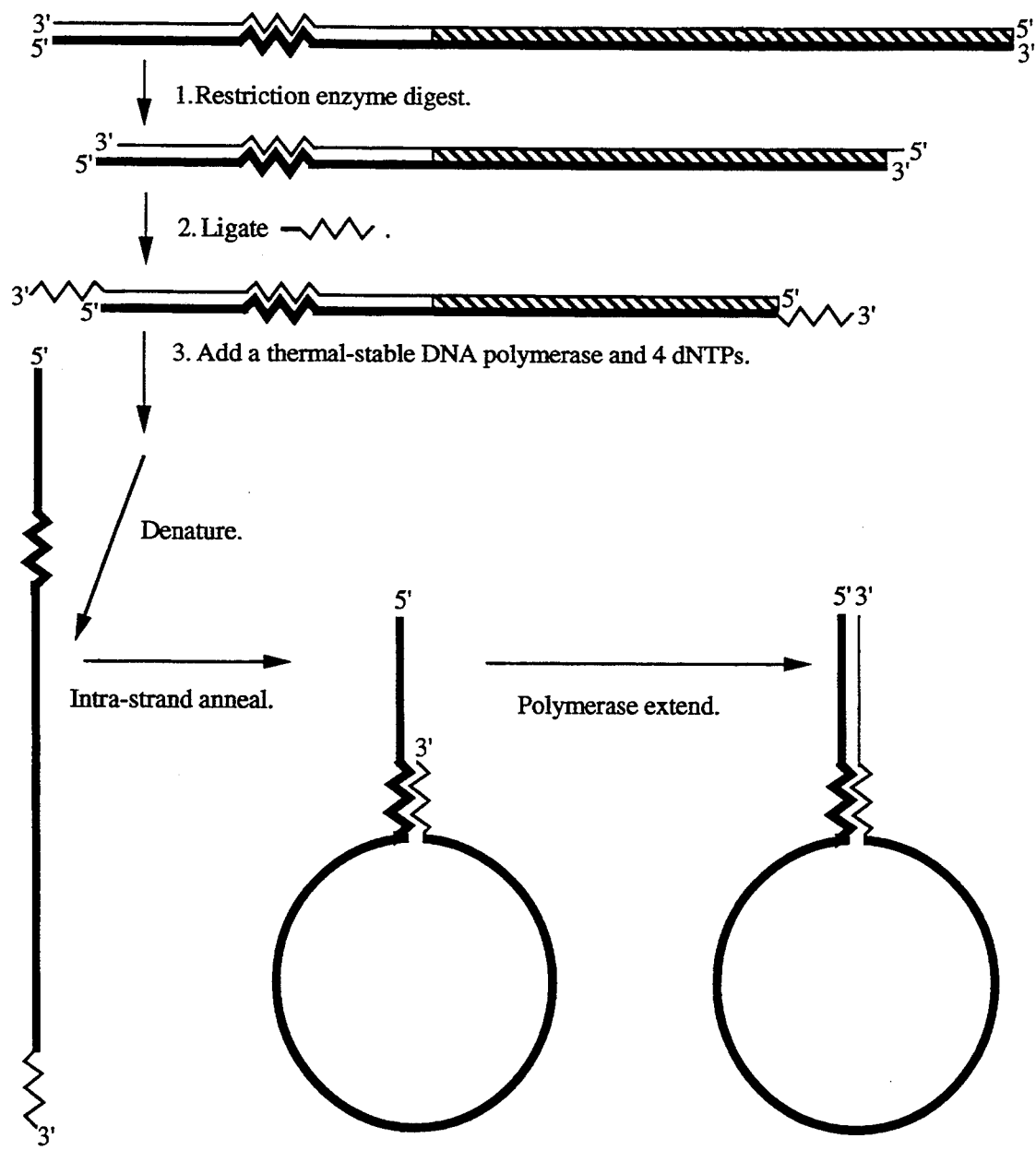
Figure 3:
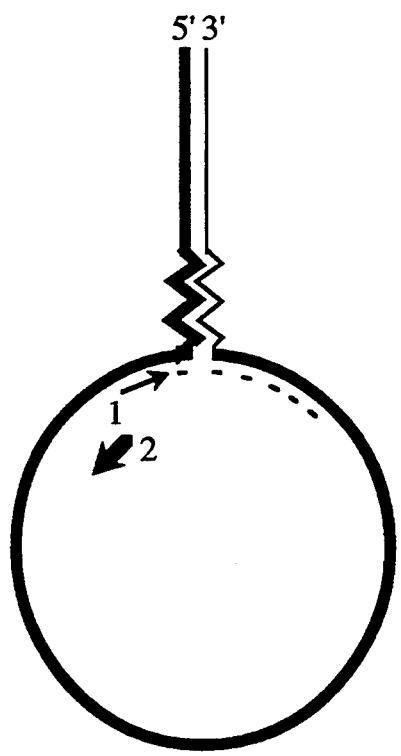
Figure 2:
Figures 1, 4:
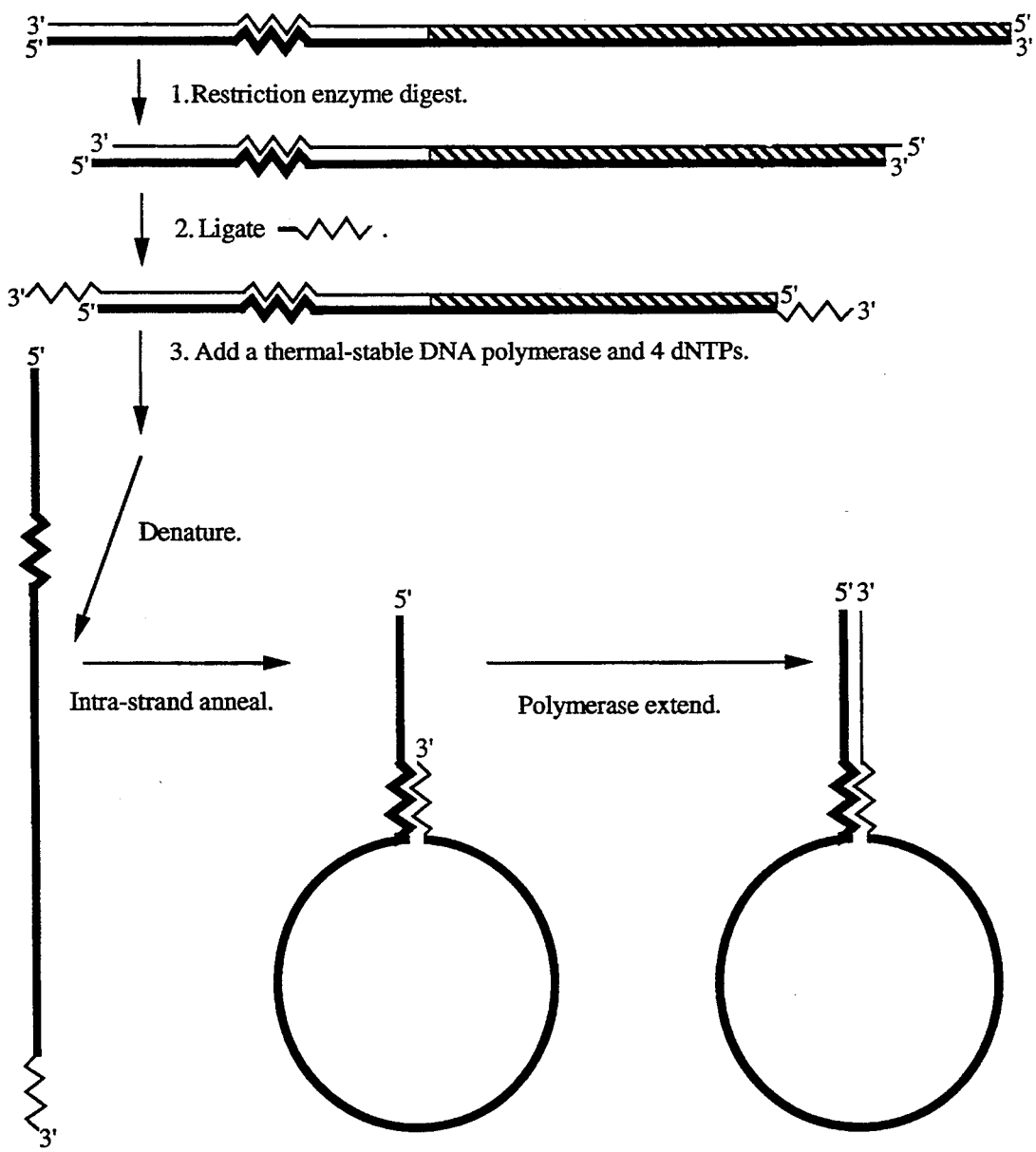
Figures 2, 4:
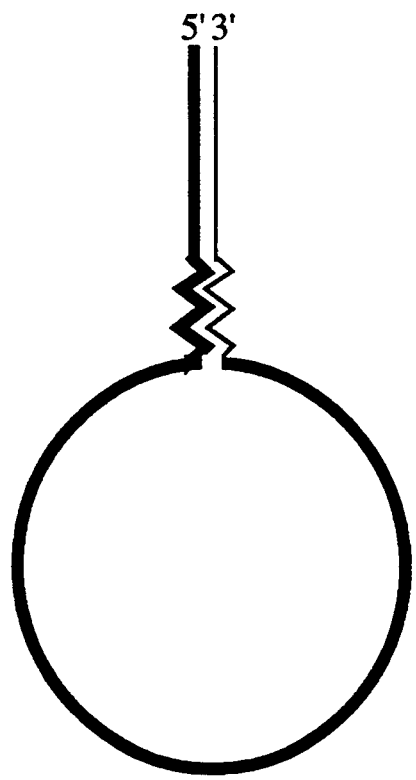

A further embodiment of the invention uses two primers (primers 1 and 2) in a PCR amplification designated herein "panhandle inverse" PCR, as shown in FIG. 3. In this embodiment primer 1 is complementary to a sequence region located between the ligated-oligonucleotide annealing site and the unknown flanking DNA, and primer 2 is homologous to a known sequence region between the sequence region complementary to primer 1 and the unknown flanking DNA. In the initial primer extension by using Taq polymerase, primer 1 polymerizes "under the DNA stem structure", jumping from one sequence region of the strand to the adjacent sequence region, generating a template for primer 2 (see Cariello et al., Gene, 99, 105–108, 1991). The dashed line in FIG. 3 shows the direction of polymerization from primer 1. In this manner, the panhandle template is a single-stranded template for inverse PCR. Following PCR amplification with primers 1 and 2, a subsequent PCR amplification can be achieved using nested primers.

Oligonucleotides are synthesized on an Applied Biosystems 391 DNA synthesizer (Foster City, Calif.), desalted over a Sephadex G25 column, dried, and suspended in $H_2O$. Aliquots are kept at $-20°$ C. For oligonucleotide phosphorylation two μg of the oligonucleotide are incubated with 10 U of $T_4$ polynucleotide kinase (New England BioLabs, Beverly, Mass.) in kinase buffer (50 mM Tris-HCl pH 7.6, 10 mM $MgCl_2$, 1 mM ATP, 5 mM Dithiothreitol) at 37° C. for 30 min. $T_4$ polynucleotide kinase is subsequently inactivated by heating at 68° C. for 10 min, and the oligonucleotide is then aliquoted and stored at $-20°$ C. until use.

Restriction enzyme digestion, as shown in step 1 of FIGS. 1, 2, 3, and 4, is followed by calf intestinal alkaline phosphatase treatment or partial fill-in by Klenow fragment according to the following procedure. Five μg of human genomic DNA (Clontech, Palo Alto, Calif.) is digested with 40 U of Bam HI (New England BioLabs), 20 U of Avr II (New England BioLabs), or 30 U of Hind III (Boehringer Mannheim Biochemicals, Indianapolis, Ind.) in 100 μl for two hours. If the DNA is treated with calf intestinal alkaline phosphatase prior to ligation of the phosphorylated oligonucleotide, 0.05 U of calf intestinal alkaline phosphatase (Boehringer Mannheim Biochemicals, Indianapolis, Ind.) in 5 μl is added to the restriction enzyme digest, and the mixture is placed at 37° C. for 30 minutes. If the DNA undergoes partial fill-in reaction prior to ligation of phosphorylated oligonucleotide, 1 μl each of 10 mM dCTP, dATP, dTTP and 5 U of Klenow fragment in 2.5 μl (Boehringer Mannheim Biochemicals) is added directly to the restriction enzyme digest, and the digest is incubated at 23° C. for 30 minutes (Hung and Wensink, *Nucleic Acids Res.*, 12, 1863–1874, 1984).

Ligation of phosphorylated oligonucleotide, as shown in step 2 of FIGS. 1, 2, 3, and 4, is accomplished through the following procedure. The mixture undergoes glass bead extraction using Geneclean (BIO 101, La Jolla, Calif.). The DNA is suspended in 50 μl of TE buffer (10 mM Tris-HCl pH 8, 1 mM EDTA) and five 5 μl aliquots are frozen for use as non-oligonucleotide-ligated template controls in subsequent steps. The remaining 25 μl of genomic DNA is ligated to a previously 5' phosphorylated 30–35 nucleotide long single-stranded oligonucleotide whose 5' end is complementary to the single-stranded ends of genomic DNA. The genomic DNA is ligated with a fifty-fold molar excess of the phosphorylated oligonucleotide in T4 DNA ligase buffer (50 mM Tris-HCl pH 7.6, 10 mM $MgCl_2$, 0.5 mM ATP, 10 mM Dithiothreitol) using one Weiss U of T4 DNA ligase (Boehringer Mannheim Biochemicals) at 23° C. for 4 hours. The 30–33 nucleotide long 3' region of this oligonucleotide is complementary to the known region of genomic DNA. The ligation mixture undergoes Geneclean purification and is suspended in 25 μl of TE buffer.

The panhandle formation, as shown in step 3 of FIGS. 1, 2, 3, and 4, is carried out according to the following procedure. A 25 μl aliquot of 2× PCR mix (1.25 U of Taq polymerase (AmpliTaq, Perkin-Elmer Cetus, Norwalk Conn.), 100 mM KCl, 20 mM Tris-HCl pH 8.3, 3 mM $MgCl_2$, 0.02% w/v gelatin, 400 μM each dNTP; or 1 U of Vent polymerase (New England BioLabs), 20 mM KCl, 20 mM $(NH_4)_2SO_4$, 40 mM Tris-HCl pH 8.8, 6 mM $MgSO_4$, 0.2% non-ionic detergent (TRITON X-100), 200 mg/ml bovine serum albumin, 400 μM each dNTP), pre-aliquoted and stored at −20° C., is thawed, 10 μl $H_2O$ is added, and 50 μl of mineral oil is layered on top. The tube is pre-heated to 80° C. prior to addition of 2 μl of template (diluted in a total of 10 μl for ease of handling), in order to prevent nonspecific annealing and polymerization (Mullis, *PCR:Methods and Applications*, 1, 1–4, 1991). The mixture undergoes one thermocycle on a thermal cycler (Perkin Elmer Cetus) (denaturation, annealing, polymerization) followed by a transition to an 80° C. soak. Since the genomic DNA concentration is <4 ng/μl, the denaturation and reannealing steps result in intra-strand annealing of the ligated synthetic oligonucleotide to its complementary sequence in the genomic DNA (Triglia et al., *Nucleic Acids Res.*, 16, 8186, 1988). This is followed by polymerase extension of the recessed 3' end. The same steps are undergone in parallel in separate tubes with the control template (genomic DNA that has been digested but not ligated to the phosphorylated oligonucleotide), and to a reagent control containing no DNA template.

The preparation for initial PCR amplification, as represented in step 4 of FIGS. 1, 2, and 3, is as follows. To each of the three tubes, 12.5 pmoles of each primer (whether using primers 1 and 2 or just primer 1), in a total volume of 5 μl $H_2O$, is added under the mineral oil, while the tubes remained in the heat block at 80° C. This results in a final concentration of 0.25 μM for each primer with 200 μM for each dNTP.

For initial PCR amplification, as shown in step 5 of FIGS. 1, 2, and 3, all three tubes (sample, template control, reagent control) undergo 30 PCR amplification cycles.

The preparation for two primer nested PCR amplification, as represented in step 6 of FIG. 1, is as follows. One μl of the unpurified amplified PCR product is removed from each tube by inserting a long thin pipette tip through the mineral oil layer, and placed in a corresponding second set of PCR tubes containing nested primers (3 and 4) preheated to 80° C. with the same enzyme, reagents, and primer concentrations as in the first PCR amplification.

In the two primer nested PCR amplification, as shown in step 7 of FIG. 1, all three tubes with the nested primers (sample, template control, reagent control) undergo 35 PCR amplification cycles.

Nested PCR amplification can be applied to the product of the panhandle inverse PCR amplification of FIG. 3, or to the product of one primer panhandle PCR of FIG. 2.

For direct sequencing of the entire PCR product, unpurified PCR products, reamplified with primers 3 and 4, are purified over a Centricon 30 microconcentrater (Amicon, Danvers, Mass.). Then the PCR product is directly sequenced with an Applied Biosystems 373 automated DNA sequencer.

For cloning of individual PCR products, PCR products are cloned into *E. coli* using Recombination PCR (Jones and Howard, *BioTechniques*, 10, 62–66, 1991). In the Recombination PCR method, plasmid pUC19 is digested with Hind III, and 2 ng of the linearized plasmid undergoes 20 cycles of PCR amplification and modification with Taq polymerase using primers whose 5' ends have 24 nucleotides of complementarity to the 5' ends of the primers used in the nested primer PCR amplification shown in step 7 of FIG. 1. Two and a half μl of each of two crude PCR products: the PCR amplified and modified linear plasmid and the PCR product derived from the nested primers shown in step 7 of FIG. 1, are co-transfected into MAX efficiency DH5α competent *E. coli* (GIBCO BRL/Life Technologies, Gaithersburg, Md.). Transformed clones are screened for the recombinant using PCR as described (Jones and Howard, *BioTechniques*, 10, 62–66, 1991).

For sequencing of plasmid inserts, plasmids are first purified using Qiagen midi-columns (Qiagen Inc., Studio City, Calif.) following the manufacturer's instructions. Then plasmid inserts are sequenced using Sequenase Version 2.0 (United States Biochemical, Cleveland, Ohio) following the manufacturer's protocol. In another embodiment, the generation of the panhandle structure, and the existence of a thermostable DNA polymerase with a single-strand 3' exonuclease activity, such as Vent polymerase (Vent DNA polymerase technical bulletin (March 1991), New England Biolabs, Beverly, Mass.), is used to purify the panhandle structure in solution.

In a final embodiment, the materials for use in the panhandle structure purification (FIG. 4) are ideally suited for the preparation of kits. For example, a kit containing such materials can be useful in providing purified portions of DNA for cloning. Following the denaturation and reannealing that generates the panhandle structure, purification of the panhandle structure occurs as a result of the following. A mixture containing the panhandle structure, a thermal stable DNA polymerase with single-strand 3' exonuclease activity, a polymerase buffer, and 1-4 dNTPs is incubated at high temperature. The purification of the DNA strand that forms a panhandle structure occurs because the double-stranded portion of the handle protects the unknown DNA contained in the single-stranded loop, or pan portion, from exonuclease digestion by template directed polymerization. At the same time the exonuclease activity of the DNA polymerase digests the free 3' ends of extraneous strands in the originally complex mixture (Englund, *J. Biol. Chem.*, 246, 3269-3276, 1971; Sanger and Coulson, *J. Mol. Biol.*, 94,441-448, 1975). Only those few extraneous DNA sequences bracketed by a long inverted repeat sequence in a single restriction fragment have the requisite self-complementarity to be protected from the single-stranded 3' exonuclease activity of the polymerase. This permits purification in solution of unknown DNA flanking a known site in an originally complex mixture.

In the presence of 4 dNTPs, polymerization activity results in the extension and preservation of the double-stranded portion of the handle of the panhandle structure. If 1-3 dNTPs are used, 3' exonuclease activity digests the 3' end until a template base complementary to one of the dNTPs is found, at which time a base exchange reaction takes place (Englund, *J. Biol. Chem.*, 246, 3269-3276, 1971; Sanger and Coulson, *J. Mol. Biol.*, 94, 441-448, 1975). By not including all four dNTPs, other long polymerization products do not form. If a single strand of DNA is not bracketed by inverted repeats long enough to form double-stranded DNA at the high temperature tolerated by the thermal-stable DNA polymerase, it is digested. Denaturation and reannealing repeats the process.

The present invention can be combined with other methods for purification of the panhandle template. One method is by the incorporation of Biotin 11 dUTP during the formation of the double-stranded panhandle (see step 3 in FIGS. 1, 2, 3, and 4) (Lo et al., *Nucleic Acids Res.*, 16, 8719, 1988), which is followed by separation by magnetic streptavidin. Another method is by incorporation of biotinylated primers, which is followed by magnetic streptavidin mediated removal of primer extension products (Rosenthal and Jones, *Nucleic Acids Res.*, 18, 3095-3096, 1990; Syvanen et al., *Nucleic Acids Res.*, 16, 11327-11338, 1988; Mitchell and Merril, *Analytical Biochem.*, 178, 239-242, 1989).

In the context of cloning technology, the present invention facilitates the generation of contiguous yeast artificial chromosome (YAC) clones by providing a rapid and reliable method for the cloning of YAC endpoints. Such YAC endpoints make possible the ordering of large fragments of individual chromosomes cloned in YAC vectors (Riley et al., *Nucleic Acids Res.*, 18, 2887-2890, 1990; Rosenthal and Jones, *Nucleic Acids Res.*, 18, 3095-3096, 1990; Breukel et al., *Nucleic Acids Res.*, 18, 3097, 1990; Ochman et al., *PCR Protocols—A Guide to Methods and Applications.* Academic Press, San Diego, Calif. pp. 219-227, 1990). The present invention also provides a method for amplifying and sequencing successive, overlapping fragments of YAC inserts. Sequence artifacts have been associated with cloning in prokaryotic vectors (Ishiura et al., *J. Gen. Microb.*, 136, 69-79, 1990), and with the cloning of chromosome fragments into YAC vectors (Neil et al., *Nucleic Acids Res.*, 18, 1421-1428, 1990). The present invention has the potential of supplanting current cloning-based strategies for sequencing the human genome. It also permits genome walking into unclonable regions of DNA (Wyman et al, *Proc. Natl. Acad. Sci. USA.*, 82, 2880-2884, 1985).

In addition, the present invention provides an alternative method for chromosome jumping procedures. In the case of chromosome jumping, a large restriction fragment, only one side of which is known, is circularized in order to bring the region with known sequence at one end of the fragment adjacent to the region of unknown sequence at the other end of the fragment. These large circles of DNA are restriction enzyme digested with a frequent cutter that renders a single-stranded 5' overhang sequence. According to the present invention, a single-stranded oligonucleotide is ligated to the ends of the resulting fragments. This oligonucleotide is constructed to be complementary to the known region at one end of the original fragment, which is now adjacent to the unknown region of interest. Denaturation of these fragments, followed by self-annealing and template-directed polymerization, results in a DNA fragment with known DNA flanking both ends of the sequence of the unknown end of the original, large restriction fragment. This permits amplification and sequencing of this unknown end.

The present invention can also be used to generate specific linking fragments (Poustka and Lehrach, Trends in *Genet.*, 2, 174-179, 1986; Kandpal et al., *Nucleic Acids Res.*, 18, 3081, 1990). Linking fragments connect large genomic DNA fragments that have been produced following digestion by a rare cutting restriction enzyme, such as Not 1. These large fragments are separated by pulsed-field gel electrophoresis and can be cloned into YAC vectors. To obtain a specific linking fragment, the present invention can be used to amplify a short stretch of DNA adjacent to an end of one large fragment directly from genomic DNA.

Other applications of this method include: the amplification of fragments adjacent to cDNA, such as regulatory regions and intron-exon junctions, and the determination of viral and transposon integration sites. The present invention permists sidestepping traditional cloning approaches for obtaining new sequence information.

The above disclosure generally describes the present invention. A more complete understanding can be obtained by reference to the following specific examples which are proposed for purposes of illustration only, and are not intended to limit the scope of the invention.

EXAMPLE 1

AMPLIFICATION OF 305 BP DNA SEGMENT FROM HUMAN GENOMIC DNA USING PANHANDLE PCR

A region of β-globin DNA was amplified from total human genomic DNA, using four amplification primers that initially flank only one side of this sequence. A control template and reagent control were also amplified. Ten μl of each of the three PCR products from the nested primers were run on a 2% agarose gel. Only the tube that initially contained the genomic DNA following Bam H1 digestion, calf intestinal alkaline phosphatase treatment, and ligation to the phosphorylated oligonucleotide yielded a detectable product. This product migrated at the predicted 305 bp size, permitting the identification of 218 bp of "unknown" flanking genomic DNA, containing the second intron-exon junction with the last 10 bp of the first intron and the first 208 bp of the second exon (Lawn et al., Cell, 21, 647-651, 1980).

In more detail: human genomic DNA was cut with Bam Hl, treated with calf intestinal alkaline phosphatase, and ligated to the following phosphorylated oligonucleotide: GATCTTCTCTGTCTCCA CATGCCCAGTTTCTATTG (SEQ ID NO:1). The mixture underwent one thermocycle: denaturation at 94° C. for one min, a two minute transition to 60° C. for 30 sec, and then a rapid transition to an 80° C. soak. Initial PCR amplification (primer 1: AGGCCCTGGCAGGTTG-GTATC (SEQ ID NO:2); primer 2: TCCTCTTGGGTTTCTGATAGGCACTGAC (SEQ ID NO:3) (5' nucleotides not complementary to β-globin underlined)) used the following parameters for 30 cycles: 94° C. for 30 sec, 56° C. for 30 sec, 72° C. for 30 sec, followed by a final extension of 72° C. for 7 min, and then an 80° C. soak. The subsequent, nested PCR amplification (primer 3: CAAGGT-TACAAGACAGGTTTAAGGAGAC (SEQ ID NO:4); primer 4: CGTCTCTCTGCCTATTGGT-CTATTTTCC (SEQ ID NO:5) (5' nucleotides not complementary to β-globin underlined)) used identical parameters as for the initial PCR amplification, except 35 cycles.

Figure 5:
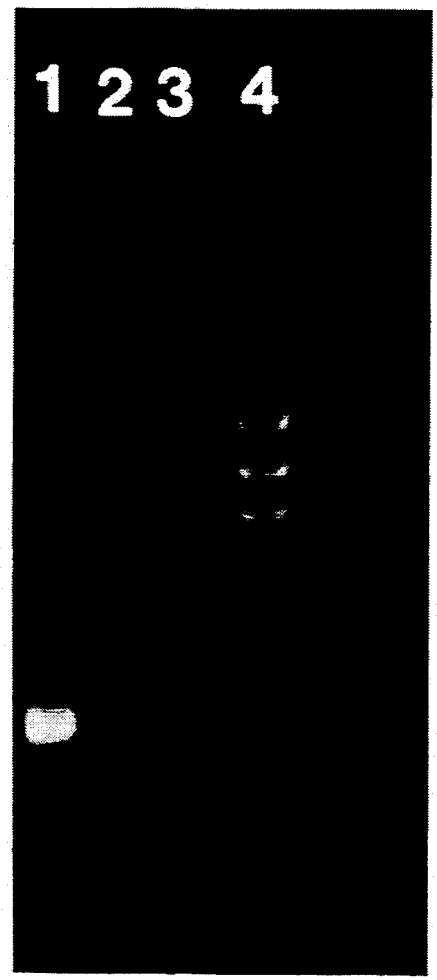
FIG. 5 shows the results of amplification of 305 bp of the human β-globin gene directly from human genomic DNA using four primers and Taq polymerase.
Figure 6:
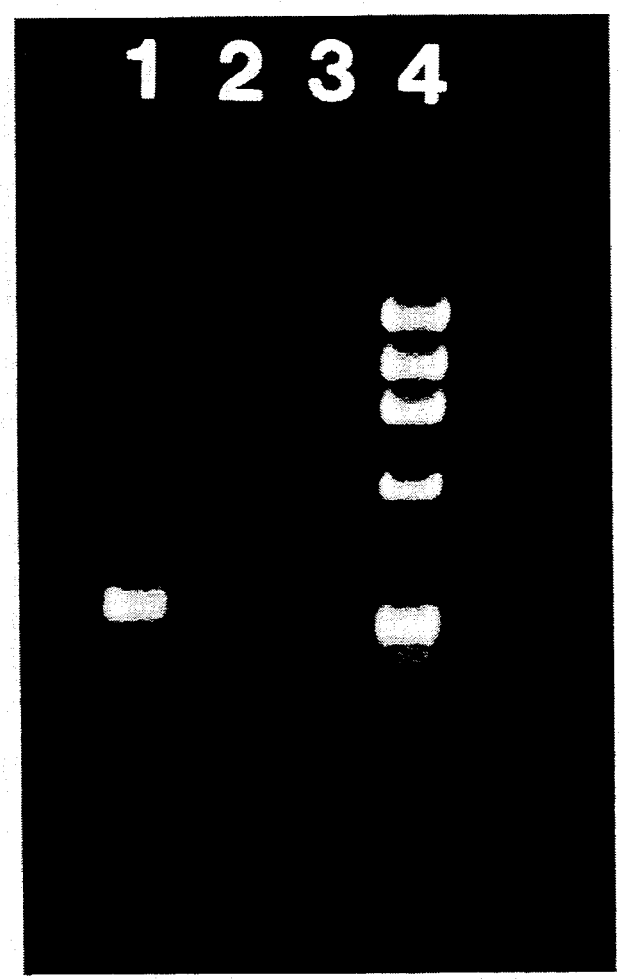
FIG. 6 shows the results of amplification of 305 bp of the human β-globin gene directly from human genomic DNA using four primers and Vent polymerase.

The results of the gels using Taq polymerase or Vent polymerase (see FIGS. 5 and 6, respectively) for generation of the panhandle and PCR amplification provided the following information. Lane 1 showed human genomic DNA after Bam H1 digestion, calf intestinal alkaline phosphatase treatment and ligation to phosphorylated oligonucleotide. Lane 2 showed human genomic DNA after Bam H1 digestion and calf intestinal alkaline phosphatase treatment without ligation to phosphorylated oligonucleotide. Lane 3 showed a control with no template. Lane 4 showed φ×174 Hae 111 MW markers. Following ethidium bromide staining, lane 1 yielded the 305 bp product of interest.

Sequence analysis of each entire PCR product confirmed its identity. Individual Taq derived products were analyzed using Recombination PCR (Jones and Howard, BioTechniques, 10, 62-66, 1991). Eleven of twelve clones tested contained the recombinant. Sequencing of the 305 bp panhandle PCR product in each of 6 clones revealed no errors in 4 clones and 2 errors in each of 2 clones (Each clone had a C for T substitution within the 218 bp of "unknown" flanking DNA; one clone also had an A to G substitution within the ligated-oligonucleotide annealing site, and the other clone had a C deleted from a sequence of 3 Cs, two of which lie within (nested) primer 4 from FIG. 1; deletion of a base in a primer sequence is a type of error previously reported in Recombination PCR (Jones and Howard, BioTechniques, 10, 62-66, 1991)).

EXAMPLE 2

AMPLIFICATION OF DNA SEGMENTS GREATER THAN 2 KB FROM HUMAN GENOMIC DNA USING PANHANDLE PCR

Fragments greater than 2 kb were also amplified using primers that initially flank only one side of the human genomic DNA. A partial fill-in reaction using Klenow fragment was done in order to convert the self-complementary ends of restriction enzyme digested genomic DNA to mutually incompatible ends, and, thereby, prevented self-ligation of the genomic DNA during the ligation to the phosphorylated oligonucleotide (Hung and Wensink, Nucleic Acids Res., 12, 1863-1874, 1984). Partial fill-in of Avr ll cut human genomic DNA with dATP, dCTP, and dTTP results in a single protruding C on the 5' ends of each double stranded fragment of Avr ll digested genomic DNA. These ends were, therefore, no longer complementary to each other, but they were complementary to the terminal 5' G of the same phosphorylated oligonucleotide that was used to amplify the 305 bp product.

Using genomic DNA, a region of β-globin DNA was amplified from total human genomic DNA using four amplification primers that initially flank only one side of this sequence. The targeted sequence was 2307 bp long and contained 2221 bp of "unknown" flanking genomic DNA, consisting of the last 10 bp of the first intron, the remaining 1333 bp of the human β-globin gene, and 878 bp of 3' sequence flanking the β-globin gene (Lawn et al., Cell, 21, 647-651, 1980). A control template and reagent control were also amplified.

In this experiment, human genomic DNA was cut with Avr ll underwent a partial fill-in reaction using Klenow fragment and dCTP, dATP and dTTP, followed by ligation to the same phosphorylated oligonucleotide as in Example 1. All primers and thermocycle parameters are the same as in Example 1, except the extension time at 72° C. in the PCR steps was extended to 2 minutes. Ten μl of each of the three PCR products from the nested primers were run on a 1% agarose gel. Only the tube that initially contained the genomic DNA following Avr ll digestion, partial fill-in with Klenow fragment, and ligation to the phosphorylated oligonucleotide yielded products close to the predicted 2307 bp product. The PCR product also contained an approximately 850 bp product.

Figure 7:
FIG. 7 shows the results of an amplification of a human β-globin gene segment greater than 2 kb directly from human genomic DNA using four primers and Taq polymerase.
Figure 8:
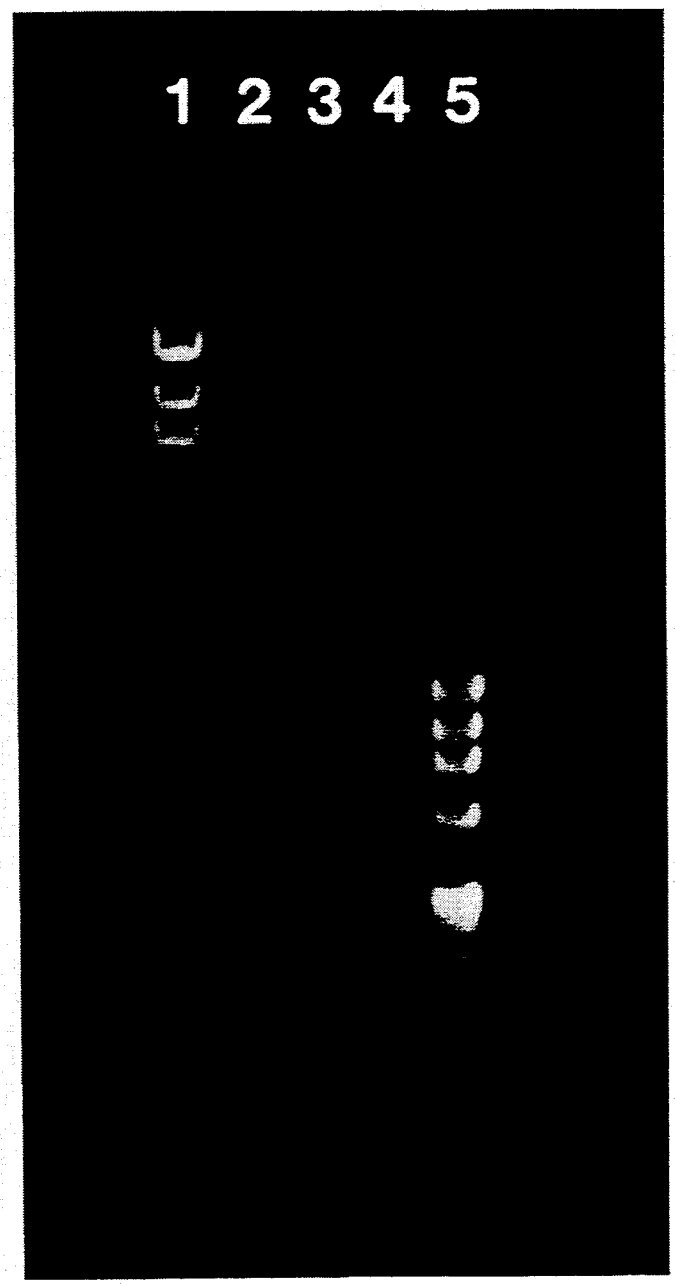
FIG. 8 shows the results of an amplification of a human β-globin gene segment greater than 2 kb directly from human genomic DNA using four primers and Vent polymerase.

The results of the gel using either Taq polymerase or Vent polymerase (see FIGS. 7 and 8, respectively) provided the following information for the human β-globin gene amplification. Lane 1 showed λ Hind lll MW markers. Lane 2 showed human genomic DNA after Avr 11 digestion, partial fill-in reaction with Klenow fragment and ligation to phosphorylated oligonucleotide. Lane 3 showed human genomic DNA after Avr ll digestion and partial fill-in reaction with Klenow fragment without ligation to phosphorylated oligonucleotide. Lane 4 showed a control with no template. Lane 5 showed φ×174 Hae lll MW markers. Following ethidium bromide staining, only lane 2 yielded products greater than 2 kb.

In order to characterize these panhandle PCR products, individual Taq derived products were cloned using Recombination PCR (Jones and Howard, BioTechniques, 10, 62-66. 1991). Eleven of twelve clones tested contained an approximately 850 bp insert and one contained an approximately 2.3 kb insert. The ends of two of the 850 bp inserts and the ends of the single 2.3 kb insert were sequenced. Each of the clones sequenced contained the β-globin region of interest. In each of the three clones, the inserts were shorter than the predicted length. In addition, each insert contained short extraneous sequences between the phosphorylated oligonucleotide and the unknown DNA of interest. Sequencing of 230 nucleotides of the 850 bp products from the primer 4 end revealed the targeted β-globin sequence without errors except for a C deleted from the primer 4 sequence in one clone. Sequencing of 190 nucleotides of the 850 bp products from the primer 3 end revealed that one nucleotide was deleted from the ligated-oligonucleotide, followed by 6 nucleotides of unknown origin (ATAGAG), 1467 nucleotides of missing β-globin, with no errors following the sequencing of 122 nucleotides of β-globin sequence. Sequence analysis of the 2.3 kb insert revealed a product just short of the full length of targeted β-globin sequence (sequencing of 230 nucleotides from the primer 4 end revealed no errors. Sequencing of 224 nucleotides from the primer 3 end revealed that 5 nucleotides were deleted from the 5' end of the ligated-oligonucleotide, followed by 8 nucleotides (CAATATGT), 53 nucleotides of missing β-globin DNA, and then 158 nucleotides of β-globin DNA, with one error, a T to C substitution). In each of the three clones, the DNA that lies adjacent to the "known" region, sequenced from the primer 4 containing end, was intact. Extraneous sequences were appended to the far end of the "unknown" DNA, adjacent to the ligated oligonucleotide. These short extraneous sequences did not lie with the "unknown flanking" DNA.

In order to obtain the full length product, Avr ll digested human genomic DNA was treated with calf intestinal alkaline phosphatase and ligated to an oligonucleotide identical to the preceding phosphorylated oligonucleotide except for its 5' end. This 5' end was complementary to the 4 nucleotides extending from each strand of digested DNA. A control template and reagent control were also amplified. Ten μl of each of the three PCR products from the nested primers were run on a 1% agarose gel. Only the tube that initially contained the genomic DNA following Avr ll digestion, calf intestinal alkaline phosphatase treatment, and ligation to the phosphorylated oligonucleotide yielded products in the range of the predicted 2307 bp product.

In more detail: a second amplification of a portion of the human β-globin gene directly from human genomic DNA used four primers that initially flank only one side of the amplified region and was run on 1% agarose gel. Human genomic DNA was cut with Avr ll, treated with calf intestinal alkaline phosphatase, and ligated to the following phosphorylated oligonucleotide: CTAGTTCTCTGTCTCCACATGCCCAGTTT-CTATTG (SEQ ID NO:6). All primers and thermocycle parameters are the same as in Example 1, except the extension time at 72° C. In both PCR amplifications was extended to 2 minutes, and the annealing temperature was 60° C. in the nested PCR amplification.

Figure 9:
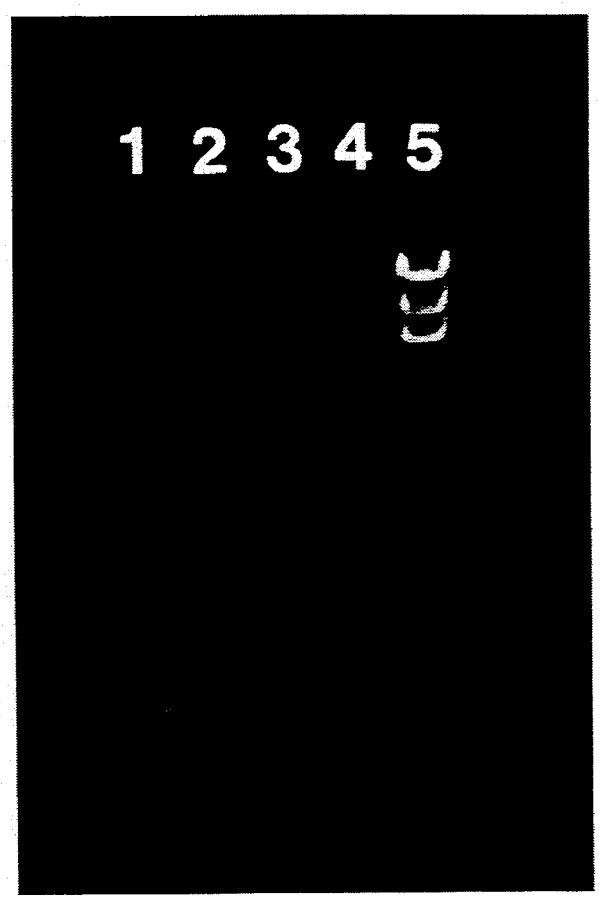
FIG. 9 shows the results of a second amplification of a human β-globin gene segment greater than 2 kb directly from human genomic DNA using four primers and Taq polymerase.

The results of the gel of FIG. 9 provided the following information for the second human β-globin gene amplification. Lane 1 showed ×174 Hae 111 MW markers. Lane 2 showed human genomic DNA after Avr ll digestion, calf intestinal alkaline phosphatase treatment, and ligation to phosphorylated oligonucleotide. Lane 3 showed human genomic DNA after Avr ll digestion and calf intestinal alkaline phosphatase treatment without ligation to phosphorylated oligonucleotide. Lane 4 showed a control with no template. Lane 5 showed λHind 111 MW markers. Following ethidium bromide staining, only lane 2 yielded products greater than 2 kb.

Individual products were cloned using Recombination PCR (Jones and Howard, *BioTechniques*, 10, 62–66, 1991). Two of six clones tested contained inserts; one 1.7 kb and the other 2.3 kb. The ends of each insert were sequenced. Sequencing of 195 nucleotides of the 1.7 kb product from the primer 4 end revealed the predicted sequence with no errors. Sequencing of 171 nucleotides of the 1.7 kb product from the primer 3 end revealed that 12 nucleotides were deleted from the 5' end of the ligated-oligonucleotide, and 569 nucleotides of the β-globin sequence were missing, with no errors following the sequencing of 120 nucleotides of β-globin. Sequencing of the ends of the 2.3 kb insert revealed the full length product of interest with only one error (From the primer 4 end, 195 nucleotides were without error. From the primer 3 end, of 199 nucleotides sequenced, there was a one nucleotide substitution in the ligated oligonucleotide). Thus, this method permitted the amplification of a large piece of flanking DNA directly from human genomic DNA.

EXAMPLE 3

AMPLIFICATION OF THE CYSTIC FIBROSIS TRANSMEMBRANE CONDUCTANCE REGULATOR (CFTR) GENE PROMOTER SEQUENCE USING PRIMERS THAT ANNEAL TO cDNA SEQUENCE USING PANHANDLE PCR

In order to assess the ability of panhandle PCR to amplify promoter sequences using cDNA data, and to evaluate the efficacy of this method on a relatively GC rich region, the CFTR gene promoter was amplified directly from human genomic DNA using cDNA sequence data (Riordan et al., *Science*, 245, 1066–1072, 1989). A single predicted 769 bp product was obtained (See FIG. 10, lane 2). This fragment contains 686 bp that flanks the primer annealing sites, including 657 bp of genomic sequence that lies 5' to the cDNA sequence. The unpurified PCR product was directly sequenced, confirming the identity of the sequence. The two published sequences of this region contain three discrepancies (Yoshimura et al., *J. Biol. Chem.*, 266, 9140–9144, 1991; Zielenski et al., *Genomics*, 10, 214–228, 1991). These differences, placing the first nucleotide of the cDNA sequence at position +1, are: an A vs G in position −500, a C vs A in position −266, and a T vs G in position −258, respectively. Our sequence differed from each of the two published sequences by containing an A in position −500, an A in position −266, and a G in position −258.

In more detail: amplification of 5' flanking region of the Cystic Fibrosis transmembrane conductance regulator directly from human genomic DNA used four primers derived from cDNA data. This was run on 2% agarose gel. Human genomic DNA was cut with Hind 111, treated with calf intestinal alkaline phosphatase, and ligated to the following phosphorylated oligonucleotide: AGCTTGAGCCCAGACGGCCCTAG-CAGGGAC (SEQ ID NO:7). The mixture underwent one thermocycle: Denaturation at 94° C. for one min, a two minute transition to 72° C. for 30 sec, and then a rapid transition to an 80° C. soak. Initial PCR amplification (primer 1: TTTGGAGACACCGCTGGCCTTTTC (SEQ ID NO:8); primer 2: (GTAATGCCAAAGACCTAC-TACTCTGGGTGC (SEQ ID NO:9) (5' nucleotide not complementary to the cystic fibrosis transmembrane conductance regulator gene underlined)) used the following parameters for 30 cycles: 94° C. for 30 sec, 60° C. for 30 sec, 72° C. for 1 min, followed by a final extension at 72° C. for 7 min, and then came to an 80° C. soak. The subsequent, nested PCR amplification (primer 3: AGGCGACCTCTGCATGGTCTCTC (SEQ ID NO:10); primer 4: GCTGCCGCTCAACCCTTTTTCTCTG (SEQ ID NO: 11) (5' nucleotide not complementary to the cystic fibrosis transmembrane conductance regulator gene underlined)) used identical parameters as for the initial PCR amplification, except 35 cycles.

Figure 10:
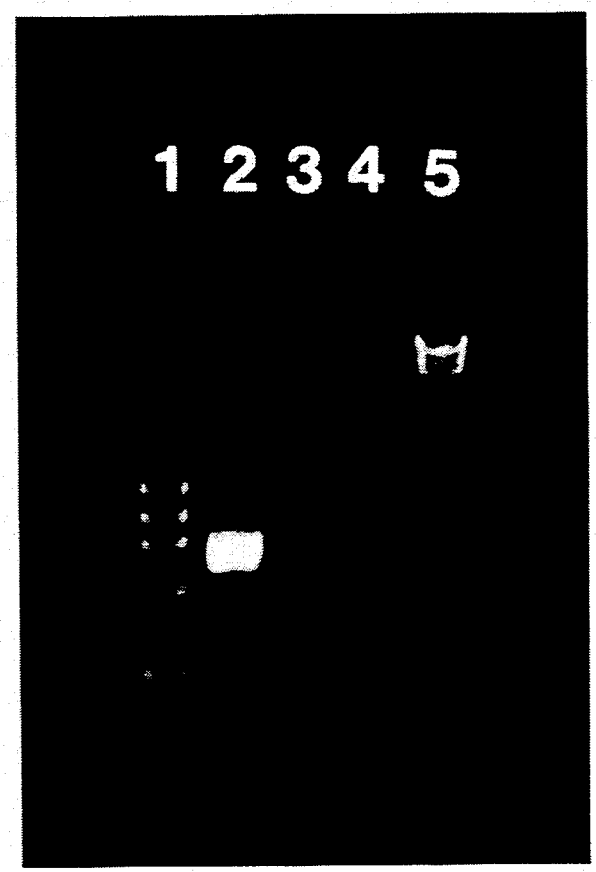
FIG. 10 shows the results of amplification of a 5' flanking region of the Cystic Fibrosis transmembrane conductance regulator directly from human genomic DNA using four primers and Taq polymerase.

The results of the gel of FIG. 10 provided the following information. Lane 1 showed ♀ ×174 Hae 111 MW markers. Lane 2 showed human genomic DNA after Hind 111 digestion, calf intestinal alkaline phosphatase treatment, and ligation to phosphorylated oligonucleotide. Lane 3 showed human genomic DNA after Hind 111 digestion and calf intestinal alkaline phosphatase treatment without ligation to phosphorylated oligonucleotide. Lane 4 showed a control with no template. Lane 5 showed λ Hind 111 MW markers. Following ethidium bromide staining, lane 2 yielded the 769 bp product of interest.

EXAMPLE 4

ONE PRIMER PANHANDLE PCR

The primer used for panhandle PCR is homologous to the sense strand of plasmid pUC19 (2686 base pairs) at nucleotides 117–133, and is placed at a concentration of 25.0 pmoles/2 μl. pUC19 is the template sequence. It is digested with Bam H1 (the restriction site for Bam H1 begins at sense nucleotide #417). A portion of this cut pUC19, to be used as the control template, is aliquoted at 1 pg/μl.

Plasmid pUC19, which has been cut with Bam H1, is treated with calf intestinal alkaline phosphatase, and then ligated to a 100 molar excess of a 5′ phosphorylated oligonucleotide (phosphorylation carried out with T4 polynucleotide kinase). The 5′ phosphorylated oligonucleotide is homologous to the antisense nucleotides 174–147 of pUC19 and has GA added to its 5′ end so that its 5′ end contains GATC, which is complementary to Bam H1 digested DNA ends. The resulting panhandle template is aliquoted at 1 pg/μl.

To a 2× PCR pre-mix (1 U of Vent polymerase (New England BioLabs), 20 mM KCl, 20 mM (NH4)2SO4, 40 mM Tris-HCl pH 8.8, 6 mM MgSO4, 0.2% non-ionic detergent (TRITON X-100), 200 μg/ml bovine serum albumin, 400 μM each dNTP, pre-aliquoted at 25 μl), add 21 μl H2O, centrifuge briefly, place mineral oil on top, and place in the heat block at 80° C. for 1 min. Then add 2 μl of template (2 pg pUC19 cut with Bam H1, treated with calf intestinal alkaline phosphatase, and ligated to the phosphorylated oligonucleotide) and undergo one thermal cycle for panhandle extension (94° C. for one min, a two minute transition to 62° C. for 30 sec, 72° C. for one min., and then go to an 80° C. soak). Also, run control tubes with 2 pg pUC19 cut only (template control) and 2 μl H2O (reagent control) for a total of three samples.

Figure 11:
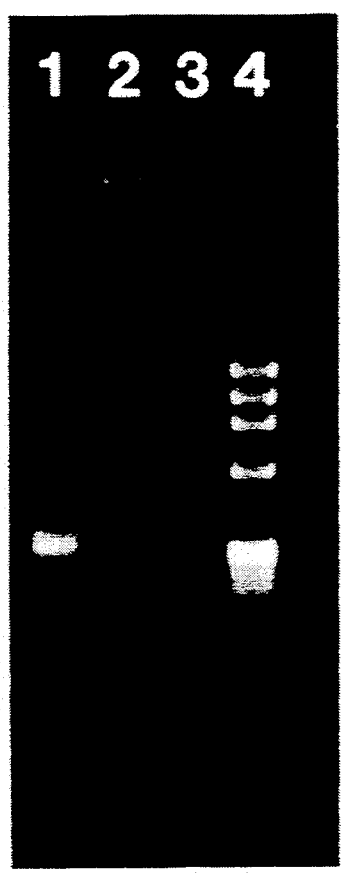
FIG. 11 shows the results of amplification of 361 bp of the plasmid pUC19 using one primer and Vent polymerase.

Add 2 μl containing 25 pg of the PCR primer to each of the three tubes while at 80° C. Place the primer under the mineral oil. Undergo 40 amplification cycles (94° C. for 30 sec., 50° C. for 30 sec., 72° C. for 1 min.), then a final 7 min. extension at 72° C. Run 9 μl of each PCR product on a 2% minigel. A 361 bp fragment is in the tube that contained pUC19 that had been cut with Bam H1, treated with calf intestinal alkaline phosphatase, and ligated to the phosphorylated oligonucleotide. FIG. 11 shows an agarose gel analysis of the oligonucleotides used in the one primer panhandle PCR. In FIG. 11, lane 1 shows pUC19 cut with Bam H1, treated with calf intestinal alkaline phosphatase, and ligated to 5′ phosphorylated oligonucleotide. Lane 2 shows pUC19 cut with Bam H1. Lane 3 represents a reagent control. Lane 4 shows Phi X Hae 111 digest molecular weight makers. A product of 361 bp was seen in lane 2.

EXAMPLE 5

PANHANDLE DNA PURIFICATION

In order to test the ability of a panhandle structure to be preserved from and purified by the 3′ single-strand exonuclease activity of Vent polymerase, 200 ng of 58 nucleotide long oligonucleotides were placed with 1 U of Vent polymerase (New England BioLabs) in Vent polymerase buffer (10 mM KCl, 10 mM (NH4)2SO4, 20 mM Tris-HCl pH 8.8, 3 mM MgSO4, 0.1% non-ionic detergent (TRITON X-100), 100 μg/ml bovine serum albumin) with 200 μM each dNTP in two separate reactions and underwent 25 thermal cycles (94° C. for 30 sec, 40° C. for 30 sec, 72° C. for 1 min) followed by 72° C. for 7 min, in 50 μl. The oligonucleotides used in the purification reaction were the following: GCACT-CTAGAGAGACGACTTGACACTGGACACGT-GAGATCGTCCAGTGTCAAGTCGTC (SEQ ID NO:12) (regions of self-complementarity underlined) and GCACTCTAGAGAGACGACTTGACACT-GGA CACGTGAGATCCTGCTGAACTGT-GACCTG (SEQ ID NO:13) (non-self- complementary oligonucleotide).

Figure 12:
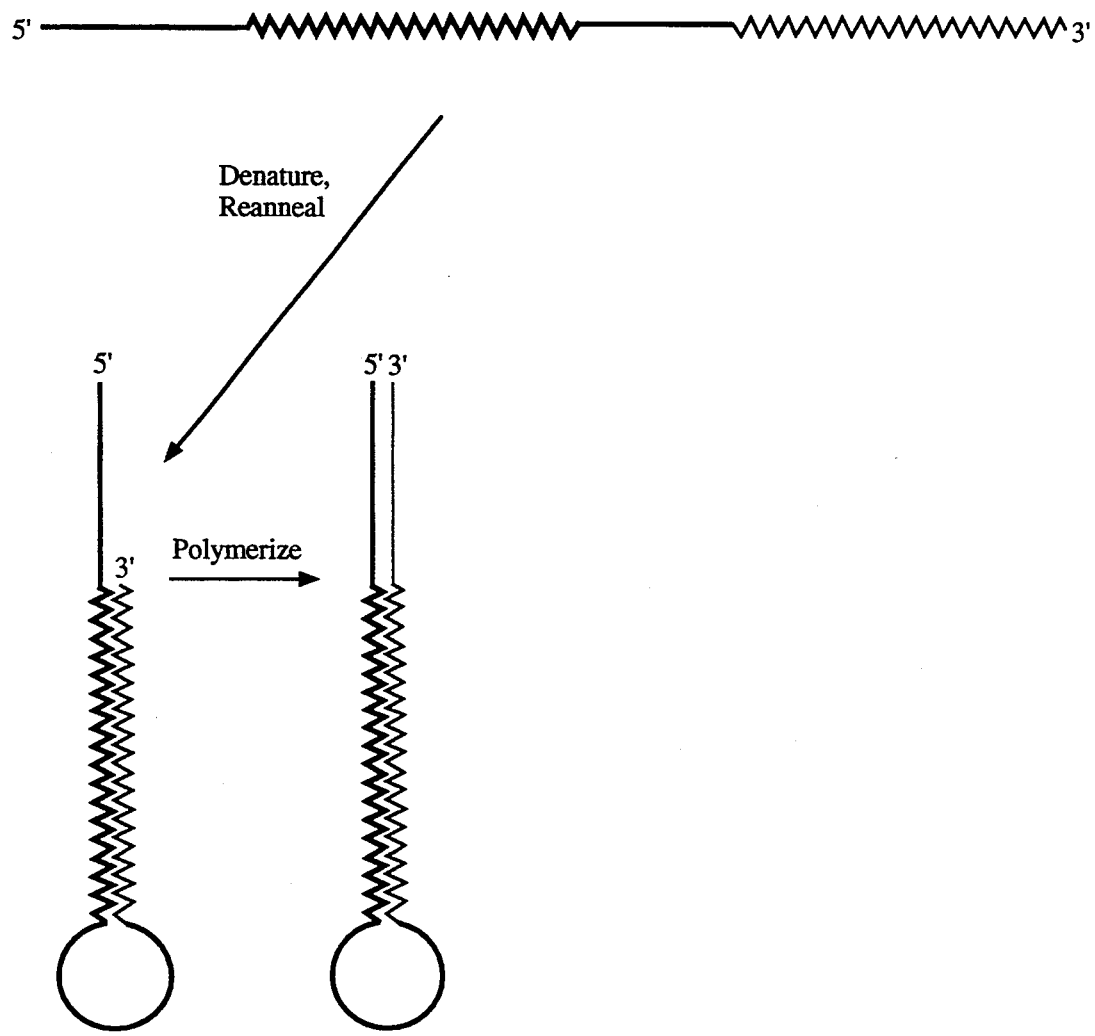
FIG. 12 is a schematic representation of a single-stranded synthetic oligonucleotide with a region of self-complementarity used in the purification of a panhandle template.

As shown in FIG. 12, the use of a single-stranded synthetic ologonucleotide with a region of self-complementarity demonstrates the purification of a panhandle template in solution by the single-strand 3′ exonuclease activity of Vent polymerase. One of the oligonucleotides, as shown in FIG. 12, has an 18 nucleotide long 3′ end that is complementary to an internal region of that oligonucleotide, such that upon self annealing it forms a panhandle structure. Polymerization from the recessed 3′ end of the double-stranded portion of the handle of the panhandle structure generates a panhandle template, which is protected from the single-strand 3′ exonuclease activity of Vent polymerase by template-directed polymerization. The other oligonucleotide, not shown in FIG. 12, has the same nucleotide composition as the first oligonucleotide, but contains no region of self complementarity, so that it is digested by Vent polymerase. Therefore, the self-complementary oligonucleotide becomes longer, while the oligonucleotide lacking self-complementary is digested by Vent polymerase. The self-complementary oligonucleotide simulates the end-modified restriction enzyme fragment containing the unknown DNA of interest; the single-stranded loop simulating unknown DNA. The non-self-complementary oligonucleotide simulates the extraneous strands that are digested using the single-strand 3′ exonuclease activity of Vent polymerase.

Figure 13:
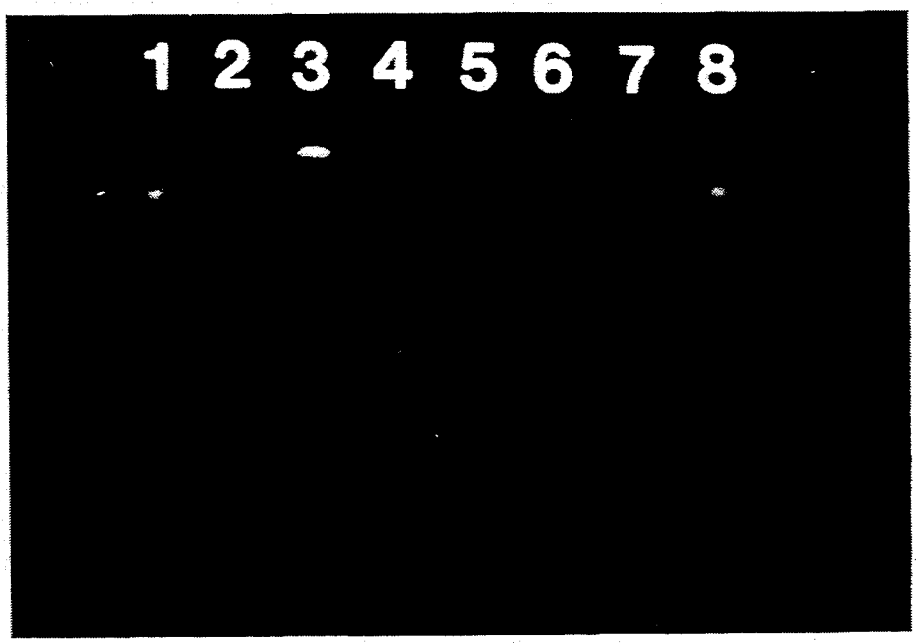
FIG. 13 shows the results of the denaturing acrylamide gel analysis of single-strand oligonucleotides used in the purification of a panhandle template.

FIG. 13 shows the results from a denaturing acrylamide gel analysis of the single-strand oligonucleotides. In FIG. 13, lanes 1 and 8 show 22 nucleotide and 55 nucleotide long single-stranded oligonucleotides functioning as molecular weight markers. Lanes 2, 4, and 6 show the self-complementary oligonucleotide. Lanes 3, 5, and 7 show the non-self-complementary oligonucleotide. Lanes 2 and 3 show 200 ng of oligonucleotides before they undergo any manipulation. The self-complementary oligonucleotide in lane 2 runs slower under these conditions. Lanes 4 and 5 show 65 ng of oligonucleotide following thermal-cycling with Taq polymerase. Lanes 6 and 7 show 65 ng of oligonucleotide following thermal-cycling with Vent polymerase. Polymerization by either Vent or Taq polymerase increased the length of the self-complementary oligonucleotide (comparing lanes 4 and 6 to lane 2). The non-self-complementary oligonucleotide was digested by Vent polymerase (lane 7).

The invention now being fully described, it will be apparent to one of ordinary skill in the art that many changes and modifications can be made without departing from the spirit or scope of the invention.

What is claimed is:

1. A method for amplification of an unknown DNA sequence that flanks a known DNA sequence, comprising the steps of:
    (a) digesting a double-stranded DNA fragment with a restriction enzyme to yield 5' nucleotide overhang sequences, wherein said DNA fragment comprises a region of known DNA sequence and a region of unknown flanking DNA sequence to be amplified;
    (b) ligating a 5' phosphorylated single-stranded oligonucleotide whose 5' end is complementary to the cohesive ends generated in step (a) of said double-stranded DNA fragment to yield 3' nucleotide overhang sequences complementary to a sequence portion within said known sequence region of said DNA fragment, wherein said sequence portion is an annealing site for said 3' nucleotide overhang sequences;
    (c) denaturing said 3' end-modified DNA fragment to produce single-stranded fragments containing said 3' nucleotide overhang sequences;
    (d) intra-strand annealing of a 3' nucleotide overhang sequence to said annealing site within said known sequence region of a single-stranded fragment, wherein said single-stranded fragment is a fragment containing said annealing site located upstream (5') to said unknown flanking sequence region, to form a single-stranded loop, or pan portion, with a double-stranded portion of an otherwise single-stranded handle, of a panhandle structure;
    (e) extending the recessed 3' end of said double-stranded portion of said handle with DNA polymerase to elongate said double-stranded portion of said handle of said panhandle structure; and
    (f) performing a polymerase chain reaction using a set of oligonucleotide primers including a primer 1 annealing to said extended 3' end strand of step (e) of said double-stranded panhandle structure and homologous to a known sequence region upstream (5') from said annealing site for said 3' nucleotide overhang sequences and a primer 2 homologous to a known sequence region both upstream (5') from said unknown flanking sequence region and downstream (3') from said annealing site for said 3' nucleotide overhang sequences.

2. The method of claim 1, further performing a second stage polymerase chain reaction to produce a nested primer product using a second set of oligonucleotide primers including a primer 3 homologous to a known sequence region both upstream (5') from said annealing site for said 3' nucleotide overhang sequences and downstream (3') from said known sequence region homologous to primer 1 and a primer 4 homologous to a known sequence region both upstream (5') from said unknown flanking sequence region and downstream (3') from said known sequence region homologous to primer 2 wherein primer 3 anneals upstream (5') from the annealing site for primer 1 on the PCR product of step (f) of claim 1, and primer 4 anneals upstream (5')

from the annealing site for primer 2 on the PCR product of step (f) of claim 1.

3. The method of claim 1, wherein said double-stranded DNA is genomic.

4. The method of claim 1, wherein primer 2 has 1 to 30 nucleotides at its 5' end that is not homologous to said known sequence region undergoing said polymerase chain reaction.

5. The method of claim 2, wherein primer 4 has 1 to 30 nucleotides at its 5' end that is not homologous to said known sequence region undergoing said second stage polymerase chain reaction.

6. The method of claim 1, wherein said region of known sequence is an insertion element and said region of unknown flanking DNA sequence to be amplified is an integration site for said insertion element and flanking regions thereof.

7. The method of claim 6, wherein said insertion element is a viral insertion element or a transposon insertion element.

8. The method of claim 1, wherein said region of known sequence is a cDNA and said region of unknown flanking DNA sequence to be amplified is from a 3' or 5' flanking region, intron-exon junction, or intron.

9. The method of claim 1, wherein said region of known sequence is a cloning vector arm and said region of unknown flanking DNA sequence to be amplified is the cloned DNA sequence lying adjacent said arm.

10. The method of claim 9, wherein said cloning vector is a yeast artificial chromosome.

11. The method of claim 1, wherein step (d) ends with incubating a mixture containing said panhandle structure with a DNA polymerase having single-stranded 3' exonuclease activity in polymerase buffer with 1-4 dNTPs wherein with 4 dNTPs step (e) is replaced thereby.

12. The method of claim 1, wherein step (e) ends with incubating a mixture containing said panhandle structure with a DNA polymerase having single-stranded 3' exonuclease activity in polymerase buffer with 1-4 dNTPs.

13. The method of claim 11, wherein said DNA polymerase is Vent polymerase.

14. The method of claim 11, wherein said DNA polymerase is Pfu polymerase.

15. The method of claim 12, wherein said DNA polymerase is Vent polymerase.

16. The method of claim 12, wherein said DNA polymerase is Pfu polymerase.

17. A method for amplification of an unknown DNA sequence that flanks a known DNA sequence, comprising the steps of:
  (a) digesting a double-stranded DNA fragment with a restriction enzyme to yield 5' nucleotide overhang sequences, wherein said DNA fragment comprises a region of known DNA sequence and a region of unknown flanking DNA sequence to be amplified;
  (b) ligating a 5' phosphorylated single-stranded oligonucleotide whose 5' end is complementary to the cohesive ends generated in step (a) of said double-stranded DNA fragment to yield 3' nucleotide overhang sequences complementary to a sequence portion within said known sequence region of said DNA fragment, wherein said sequence portion is an annealing site for said 3' nucleotide overhang sequences;
  (c) denaturing said 3' end-modified DNA fragment to produce single-stranded fragments containing said 3' nucleotide overhang sequences;
  (d) intra-strand annealing of a 3' nucleotide overhang sequence to said annealing site within said known sequence region of a single-stranded fragment, wherein said single-stranded fragment is a fragment containing said annealing site located upstream (5') to said unknown flanking sequence region, to form a single-stranded loop, or pan portion, with a double-stranded portion of an otherwise single-stranded handle, of a panhandle structure;
  (e) extending the recessed 3' end of said double-stranded portion of said handle with DNA polymerase to elongate said double-stranded portion of said handle of said panhandle structure; and
  (f) performing a polymerase chain reaction using an oligonucleotide primer 1 annealing to said extended 3' nucleotide end strand of step (e) of said double-stranded panhandle structure and homologous to a known sequence region upstream (5') from said annealing site for said 3' nucleotide overhang sequences.

18. The method of claim 17, further performing a second stage polymerase chain reaction to produce a nested primer product using an oligonucleotide primer 2 homologous to a known sequence region both upstream (5') from said annealing site for said 3' nucleotide overhang sequences and downstream (3') from said known sequence region homologous to primer 1.

19. The method of claim 17, wherein said double-stranded DNA is genomic.

20. The method of claim 17, wherein said region of known sequence is an insertion element and said region of unknown flanking DNA sequence to be amplified is an integration site for said insertion element and flanking regions thereof.

21. The method of claim 20, wherein said insertion element is a viral insertion element or a transposon insertion element.

22. The method of claim 17, wherein said region of known sequence is a cDNA and said region of unknown flanking DNA sequence to be retrieved is from a 3' or 5' flanking region, intron-exon junction, or intron.

23. The method of claim 17, wherein said region of known sequence is a cloning vector arm and said region of unknown flanking DNA sequence to be amplified is the cloned DNA sequence lying adjacent said arm.

24. The method of claim 23, wherein said cloning vector is a yeast artificial chromosome.

25. The method of claim 17, wherein step (d) ends with incubating a mixture containing said panhandle structure with a DNA polymerase having single-stranded 3' exonuclease activity in polymerase buffer with 1-4 dNTPs wherein with 4 dNTPs step (e) is replaced thereby.

26. The method of claim 17, wherein step (e) ends with incubating a mixture containing said panhandle structure with a DNA polymerase having single-stranded 3' exonuclease activity in polymerase buffer with 1-4 dNTPs.

27. The method of claim 25, wherein said DNA polymerase is Vent polymerase.

28. The method of claim 25, wherein said DNA polymerase is Pfu polymerase.

29. The method of claim 26, wherein said DNA polymerase is Vent polymerase.

30. The method of claim 26, wherein said DNA polymerase is Pfu polymerase.

31. A method for amplification of an unknown DNA sequence that flanks a known DNA sequence, comprising the steps of:
  (a) digesting a double-stranded DNA fragment with a restriction enzyme to yield 5' nucleotide overhang sequences, wherein said DNA fragment comprises a region of known DNA sequence and a region of unknown flanking DNA sequence to be amplified;
  (b) ligating a 5' phosphorylated single-stranded oligonucleotide whose 5' end is complementary to the cohesive ends generated in step (a) of said double-stranded DNA fragment to yield 3' nucleotide overhang sequences complementary to a sequence portion within said known sequence region of said DNA fragment, wherein said sequence portion is an annealing site for said 3' nucleotide overhang sequences;
  (c) denaturing said 3' end-modified DNA fragment to produce single-stranded fragments containing said 3' nucleotide overhang sequences;
  (d) intra-strand annealing of a 3' nucleotide overhang sequence to said annealing site within said known sequence region of a single-stranded fragment, wherein said single-stranded fragment is a fragment containing said annealing site located upstream (5') to said unknown flanking sequence region, to form a single-stranded loop, or pan portion, with a double-stranded portion of an otherwise single-stranded handle, of a panhandle structure;
  (e) extending the recessed 3' end of said double-stranded portion of the handle with DNA polymerase to elongate the double-stranded portion of the handle of the panhandle structure; and
  (f) performing a polymerase chain reaction using a set of oligonucleotide primers including a primer 1 annealing to said single-stranded loop of step (d) and complementary to a known sequence region both upstream (5') from said unknown flanking sequence region and downstream (3') from said annealing site for said 3' nucleotide overhang sequences and a primer 2 homologous to a known sequence region both upstream (5') from said unknown flanking sequence region and downstream (3') from said known sequence region complementary to primer 1, wherein primer 1 by primer extension under said double-stranded portion of said panhandle structure using Taq polymerase jumps from one region of said single-stranded loop to an adjacent region of said single-stranded loop to generate a linear template for primer 2.

32. The method of claim 31, further performing a second stage polymerase chain reaction to produce a nested primer product using a second set of oligonucleotide primers including a primer 3 complementary to a known sequence region both downstream (3') from said annealing site for said 3' nucleotide overhang sequences and upstream (5') from said known sequence region complementary to primer 1 and a primer 4 homologous to a known sequence region both upstream (5'') from said unknown flanking sequence region and downstream (3') from said known sequence region homologous to primer 2.

33. The method of claim 31, wherein said double-stranded DNA is genomic.

34. The method of claim 31, wherein primer 2 has 1 to 30 nucleotides at its 5' end that is not homologous to said known sequence region undergoing said polymerase chain reaction.

35. The method of claim 32, wherein primer 4 has 1 to 30 nucleotides at its 5' end that is not homologous to said known sequence region undergoing said second stage polymerase chain reaction.

36. The method of claim 31, wherein said region of known sequence is an insertion element and said region of unknown flanking DNA sequence to be amplified is an integration site for said insertion element and flanking regions thereof.

37. The method of claim 36, wherein said insertion element is a viral insertion element or a transposon insertion element.

38. The method of claim 31, wherein said region of known sequence is a cDNA and said region of unknown flanking DNA sequence to be amplified is from a 3' or 5' flanking region, intron-exon junction, or intron.

39. The method of claim 31, wherein said region of known sequence is a cloning vector arm and said region of unknown flanking DNA sequence to be amplified is the cloned DNA sequence lying adjacent said arm.

40. The method of claim 39, wherein said cloning vector is a yeast artificial chromosome.

41. The method of claim 31, wherein step (d) ends with incubating a mixture containing said panhandle structure with a DNA polymerase having single-stranded 3' exonuclease activity in polymerase buffer with 1–4 dNTPs wherein with 4 dNTPs step (e) is replaced thereby.

42. The method of claim 31, wherein step (e) ends with incubating a mixture containing said panhandle structure with a DNA polymerase having single-stranded 3' exonuclease activity in polymerase buffer with 1–4 dNTPs.

43. The method of claim 41, wherein said DNA polymerase is Vent polymerase.

44. The method of claim 41, wherein said DNA polymerase is Pfu polymerase.

45. The method of claim 42, wherein said DNA polymerase is Vent polymerase.

46. The method of claim 42, wherein said DNA polymerase is Pfu polymerase.

47. A method for purification of a DNA strand by generation of a panhandle structure, comprising the steps of:
  (a) digesting a double-stranded DNA fragment with a restriction enzyme to yield 5' nucleotide overhang sequences;
  (b) ligating a 5' phosphorylated single-stranded oligonucleotide whose 5' end is complementary to the cohesive ends generated in step (a) of said double-stranded DNA fragment to yield 3' nucleotide overhang sequences complementary to a sequence portion within said DNA fragment, wherein said sequence portion is an annealing site for said 3' nucleotide overhang sequences;
  (c) denaturing said 3' end-modified DNA fragment to produce single-stranded fragments containing said 3' nucleotide overhang sequences;
  (d) intra-strand annealing of a 3' nucleotide overhang sequence to said annealing site of a single-stranded fragment to form a single-stranded loop, or pan portion, with a double-stranded stem of an otherwise single-stranded handle, of a panhandle structure;
  (e) extending the recessed 3' end of said double-stranded stem of said handle with DNA polymerase to elongate said double-stranded stem of said handle of said panhandle structure; and (f) incubating a mixture containing said panhandle structure with a DNA polymerase having single-stranded 3' exonuclease activity in polymerase buffer with 1–4 dNTPs.

48. The method of claim 47, wherein said DNA polymerase is Vent polymerase.

49. The method of claim 47, wherein said DNA polymerase is Pfu polymerase.

50. A method for purification of a DNA strand by generation of a panhandle structure, comprising the steps of:

(a) digesting a double-stranded DNA fragment with a restriction enzyme to yield 5' nucleotide overhang sequences;

(b) ligating a 5' phosphorylated single-stranded oligonucleotide whose 5' end is complementary to the cohesive ends generated in step (a) of said double-stranded DNA fragment to yield 3' nucleotide overhang sequences complementary to a sequence portion within said DNA fragment, wherein said sequence portion is an annealing site for said 3' nucleotide overhang sequences;

(c) denaturing said 3' end-modified DNA fragment to produce single-stranded fragments containing said 3' nucleotide overhang sequences;

(d) intra-strand annealing of a 3' nucleotide overhang sequence to said annealing site of a single-stranded fragment to form a single-stranded loop, or pan portion, with a double-stranded stem of an otherwise single-stranded handle, of a panhandle structure; and (e) incubating a mixture containing said panhandle structure of step (d) with a DNA polymerase having single-single stranded 3' exonuclease activity in polymerase buffer with 1–4 dNTPs.

51. The method of claim 50, wherein said DNA polymerase is Vent polymerase.

52. The method of claim 50, wherein said DNA polymerase is Pfu polymerase.

* * * * *